US012758618B2

(12) United States Patent
Gearing et al.

(10) Patent No.: US 12,758,618 B2
(45) Date of Patent: Oct. 13, 2026

(54) COMPOSITIONS FOR TREATING RESPIRATORY TRACT INFECTION AND USES THEREOF

(71) Applicant: Lateral IP Pty Ltd, Melbourne (AU)

(72) Inventors: Andrew Gearing, Melbourne (AU); David Kenley, Melbourne (AU)

(73) Assignee: Lateral IP Pty Ltd, Melbourne (AU)

( * ) Notice: Subject to any disclaimer, the term of this patent is extended or adjusted under 35 U.S.C. 154(b) by 919 days.

(21) Appl. No.: 17/911,972

(22) PCT Filed: Mar. 16, 2021

(86) PCT No.: PCT/AU2021/050229
§ 371 (c)(1),
(2) Date: Sep. 15, 2022

(87) PCT Pub. No.: WO2021/184062
PCT Pub. Date: Sep. 23, 2021

(65) Prior Publication Data

US 2023/0256059 A1 Aug. 17, 2023

(30) Foreign Application Priority Data

| | | | |
|---|---|---|---|
| Mar. 16, 2020 | (AU) | ................................ | 2020900807 |
| Mar. 17, 2020 | (AU) | ................................ | 2020900818 |
| Nov. 16, 2020 | (AU) | ................................ | 2020904226 |

(51) Int. Cl.

| | |
|---|---|
| ***A61K 38/04*** | (2006.01) |
| ***A61K 9/00*** | (2006.01) |
| ***A61K 38/08*** | (2019.01) |
| ***A61K 38/27*** | (2006.01) |
| ***A61P 31/00*** | (2006.01) |
| ***A61P 31/16*** | (2006.01) |
| ***C07K 14/61*** | (2006.01) |

(52) U.S. Cl.
CPC ............ *A61K 38/27* (2013.01); *A61K 9/0053* (2013.01); *A61P 31/16* (2018.01)

(58) Field of Classification Search
CPC ........ A61K 38/04; A61K 38/08; A61K 38/27; A61K 9/0053; A61P 31/00; A61P 31/16; C07K 14/61
See application file for complete search history.

(56) References Cited

U.S. PATENT DOCUMENTS

| | | | |
|---|---|---|---|
| 2020/0390850 | A1 | 12/2020 | Gearing et al. |
| 2021/0130410 | A1 | 5/2021 | Gearing |
| 2022/0160815 | A1 | 5/2022 | Kenley |
| 2022/0354929 | A1 | 11/2022 | Gearing |

FOREIGN PATENT DOCUMENTS

| | | | | |
|---|---|---|---|---|
| WO | WO-2013/082667 A1 | | 6/2013 | |
| WO | WO-2019/136528 A1 | | 7/2019 | |
| WO | WO-2021127752 A1 | * | 7/2021 | ........... G01N 33/566 |

OTHER PUBLICATIONS

U.S. Appl. No. 17/788,845, filed Jun. 24, 2022, Lateral IP Pty Ltd.
Stier, H. et al., 'Safety and Tolerability of the Hexade capeptide AOD9604 in Humans', J Endocrinol Metab. 2013;3(1-2):7-15. doi:http://dx.doi.org/10.4021/jem157wX whole document, p. 14, p. 12 col. 1, p. 8 col. 1.

* cited by examiner

*Primary Examiner* — Julie Ha
(74) *Attorney, Agent, or Firm* — Foley & Lardner LLP

(57) ABSTRACT

Methods of treating a respiratory tract infection in a subject by administering to the subject in need thereof a therapeutically effective amount of C-terminal fragments of growth hormone, including LAT8881, otherwise known as AOD9604, or LAT9991F, and pharmaceutically acceptable salts thereof, are described.

10 Claims, 5 Drawing Sheets

Specification includes a Sequence Listing.

SEQUENCE LISTING

```
<160> NUMBER OF SEQ ID NOS: 53

<210> SEQ ID NO 1
<211> LENGTH: 9
<212> TYPE: PRT
<213> ORGANISM: Homo sapiens

<400> SEQUENCE: 1

Cys Arg Ser Val Glu Gly Ser Cys Gly
1               5


<210> SEQ ID NO 2
<211> LENGTH: 16
<212> TYPE: PRT
<213> ORGANISM: Homo sapiens

<400> SEQUENCE: 2

Tyr Leu Arg Ile Val Gln Cys Arg Ser Val Glu Gly Ser Cys Gly Phe
1               5                   10                  15


<210> SEQ ID NO 3
<211> LENGTH: 15
<212> TYPE: PRT
<213> ORGANISM: Homo sapiens

<400> SEQUENCE: 3

Leu Arg Ile Val Gln Cys Arg Ser Val Glu Gly Ser Cys Gly Phe
1               5                   10                  15


<210> SEQ ID NO 4
```

<211> LENGTH: 9
<212> TYPE: PRT
<213> ORGANISM: Homo sapiens

<400> SEQUENCE: 4

Cys Arg Ser Val Glu Gly Ser Cys Gly
1 5

<210> SEQ ID NO 5
<211> LENGTH: 10
<212> TYPE: PRT
<213> ORGANISM: Homo sapiens

<400> SEQUENCE: 5

Cys Arg Ser Val Glu Gly Ser Cys Gly Phe
1 5 10

<210> SEQ ID NO 6
<211> LENGTH: 9
<212> TYPE: PRT
<213> ORGANISM: Canis lupus familiaris

<400> SEQUENCE: 6

Cys Arg Arg Phe Val Glu Ser Ser Cys
1 5

<210> SEQ ID NO 7
<211> LENGTH: 17
<212> TYPE: PRT
<213> ORGANISM: Canis lupus familiaris

<400> SEQUENCE: 7

Tyr Leu Arg Val Met Lys Cys Arg Arg Phe Val Glu Ser Ser Cys Ala
1 5 10 15

Phe

<210> SEQ ID NO 8
<211> LENGTH: 16
<212> TYPE: PRT
<213> ORGANISM: Canis lupus familiaris

<400> SEQUENCE: 8

Leu Arg Val Met Lys Cys Arg Arg Phe Val Glu Ser Ser Cys Ala Phe
1 5 10 15

<210> SEQ ID NO 9
<211> LENGTH: 11
<212> TYPE: PRT
<213> ORGANISM: Canis lupus familiaris

<400> SEQUENCE: 9

Cys Arg Arg Phe Val Glu Ser Ser Cys Ala Phe
1 5 10

<210> SEQ ID NO 10
<211> LENGTH: 10
<212> TYPE: PRT
<213> ORGANISM: Canis lupus familiaris

<400> SEQUENCE: 10

Cys Arg Arg Phe Val Glu Ser Ser Cys Ala
1 5 10

<210> SEQ ID NO 11

```
<211> LENGTH: 10
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is an amino acid residue selected from the
      group consisting of serine, alanine, valine, leucine, isoleucine
      and glycine
<220> FEATURE:
<221> NAME/KEY: MISC_FEATURE
<222> LOCATION: (4)..(4)
<223> OTHER INFORMATION: Xaa is arginine or lysine
<220> FEATURE:
<221> NAME/KEY: MISC_FEATURE
<222> LOCATION: (6)..(6)
<223> OTHER INFORMATION: Xaa is an amino acid residue selected from the
      group consisting of serine, alanine, valine, leucine, isoleucine
      and glycine
<220> FEATURE:
<221> NAME/KEY: MISC_FEATURE
<222> LOCATION: (7)..(7)
<223> OTHER INFORMATION: Xaa is glutamic acid or aspartic acid
<220> FEATURE:
<221> NAME/KEY: MISC_FEATURE
<222> LOCATION: (8)..(8)
<223> OTHER INFORMATION: Xaa is an amino acid residue selected from the
      group consisting of serine, alanine, valine, leucine, isoleucine
      and glycine
<220> FEATURE:
<221> NAME/KEY: MISC_FEATURE
<222> LOCATION: (9)..(9)
<223> OTHER INFORMATION: Xaa is an amino acid residue selected from the
      group consisting of serine, alanine, valine, leucine, isoleucine
      and glycine

<400> SEQUENCE: 11

Cys Arg Xaa Xaa Pro Xaa Xaa Xaa Xaa Cys
1               5                   10


<210> SEQ ID NO 12
<211> LENGTH: 2
<212> TYPE: PRT
<213> ORGANISM: Homo sapiens

<400> SEQUENCE: 12

His Ser
1


<210> SEQ ID NO 13
<211> LENGTH: 3
<212> TYPE: PRT
<213> ORGANISM: Homo sapiens

<400> SEQUENCE: 13

Gly His Ser
1


<210> SEQ ID NO 14
<211> LENGTH: 4
<212> TYPE: PRT
<213> ORGANISM: Homo sapiens

<400> SEQUENCE: 14

Pro Gly His Ser
1


<210> SEQ ID NO 15
<211> LENGTH: 5
<212> TYPE: PRT
<213> ORGANISM: Homo sapiens
```

<400> SEQUENCE: 15

Ala Pro Gly His Ser
1               5

<210> SEQ ID NO 16
<211> LENGTH: 6
<212> TYPE: PRT
<213> ORGANISM: Homo sapiens

<400> SEQUENCE: 16

Glu Ala Pro Gly His Ser
1               5

<210> SEQ ID NO 17
<211> LENGTH: 7
<212> TYPE: PRT
<213> ORGANISM: Homo sapiens

<400> SEQUENCE: 17

Ser Glu Ala Pro Gly His Ser
1               5

<210> SEQ ID NO 18
<211> LENGTH: 8
<212> TYPE: PRT
<213> ORGANISM: Homo sapiens

<400> SEQUENCE: 18

Ser Ser Glu Ala Pro Gly His Ser
1               5

<210> SEQ ID NO 19
<211> LENGTH: 9
<212> TYPE: PRT
<213> ORGANISM: Homo sapiens

<400> SEQUENCE: 19

Pro Ser Ser Glu Ala Pro Gly His Ser
1               5

<210> SEQ ID NO 20
<211> LENGTH: 10
<212> TYPE: PRT
<213> ORGANISM: Homo sapiens

<400> SEQUENCE: 20

Asp Pro Ser Ser Glu Ala Pro Gly His Ser
1               5                   10

<210> SEQ ID NO 21
<211> LENGTH: 11
<212> TYPE: PRT
<213> ORGANISM: Homo sapiens

<400> SEQUENCE: 21

Ile Asp Pro Ser Ser Glu Ala Pro Gly His Ser
1               5                   10

<210> SEQ ID NO 22
<211> LENGTH: 2
<212> TYPE: PRT
<213> ORGANISM: Homo sapiens

<400> SEQUENCE: 22

Ser Ser
1

<210> SEQ ID NO 23
<211> LENGTH: 3
<212> TYPE: PRT
<213> ORGANISM: Homo sapiens

<400> SEQUENCE: 23

Ser Ser Lys
1

<210> SEQ ID NO 24
<211> LENGTH: 4
<212> TYPE: PRT
<213> ORGANISM: Homo sapiens

<400> SEQUENCE: 24

Ser Ser Lys Phe
1

<210> SEQ ID NO 25
<211> LENGTH: 5
<212> TYPE: PRT
<213> ORGANISM: Homo sapiens

<400> SEQUENCE: 25

Ser Ser Lys Phe Ser
1 5

<210> SEQ ID NO 26
<211> LENGTH: 6
<212> TYPE: PRT
<213> ORGANISM: Homo sapiens

<400> SEQUENCE: 26

Ser Ser Lys Phe Ser Trp
1 5

<210> SEQ ID NO 27
<211> LENGTH: 7
<212> TYPE: PRT
<213> ORGANISM: Homo sapiens

<400> SEQUENCE: 27

Ser Ser Lys Phe Ser Trp Asp
1 5

<210> SEQ ID NO 28
<211> LENGTH: 8
<212> TYPE: PRT
<213> ORGANISM: Homo sapiens

<400> SEQUENCE: 28

Ser Ser Lys Phe Ser Trp Asp Glu
1 5

<210> SEQ ID NO 29
<211> LENGTH: 9
<212> TYPE: PRT
<213> ORGANISM: Homo sapiens

<400> SEQUENCE: 29

Ser Ser Lys Phe Ser Trp Asp Glu Tyr 1 5

<210> SEQ ID NO 30
<211> LENGTH: 10
<212> TYPE: PRT
<213> ORGANISM: Homo sapiens

<400> SEQUENCE: 30

Ser Ser Lys Phe Ser Trp Asp Glu Tyr Glu
1 5 10

<210> SEQ ID NO 31
<211> LENGTH: 11
<212> TYPE: PRT
<213> ORGANISM: Homo sapiens

<400> SEQUENCE: 31

Ser Ser Lys Phe Ser Trp Asp Glu Tyr Glu Gln
1 5 10

<210> SEQ ID NO 32
<211> LENGTH: 12
<212> TYPE: PRT
<213> ORGANISM: Homo sapiens

<400> SEQUENCE: 32

Ser Ser Lys Phe Ser Trp Asp Glu Tyr Glu Gln Tyr
1 5 10

<210> SEQ ID NO 33
<211> LENGTH: 13
<212> TYPE: PRT
<213> ORGANISM: Homo sapiens

<400> SEQUENCE: 33

Ser Ser Lys Phe Ser Trp Asp Glu Tyr Glu Gln Tyr Lys
1 5 10

<210> SEQ ID NO 34
<211> LENGTH: 14
<212> TYPE: PRT
<213> ORGANISM: Homo sapiens

<400> SEQUENCE: 34

Ser Ser Lys Phe Ser Trp Asp Glu Tyr Glu Gln Tyr Lys Lys
1 5 10

<210> SEQ ID NO 35
<211> LENGTH: 15
<212> TYPE: PRT
<213> ORGANISM: Homo sapiens

<400> SEQUENCE: 35

Ser Ser Lys Phe Ser Trp Asp Glu Tyr Glu Gln Tyr Lys Lys Glu
1 5 10 15

<210> SEQ ID NO 36
<211> LENGTH: 11
<212> TYPE: PRT
<213> ORGANISM: Homo sapiens

<400> SEQUENCE: 36

Ser Cys Arg Ser Arg Pro Val Glu Ser Ser Cys
1 5 10

<210> SEQ ID NO 37
<211> LENGTH: 10
<212> TYPE: PRT
<213> ORGANISM: Homo sapiens

<400> SEQUENCE: 37

Cys Arg Ser Arg Pro Val Glu Ser Ser Cys
1               5                   10

<210> SEQ ID NO 38
<211> LENGTH: 11
<212> TYPE: PRT
<213> ORGANISM: Homo sapiens

<400> SEQUENCE: 38

Cys Arg Ser Arg Pro Val Glu Ser Ser Cys Ser
1               5                   10

<210> SEQ ID NO 39
<211> LENGTH: 12
<212> TYPE: PRT
<213> ORGANISM: Homo sapiens

<400> SEQUENCE: 39

Ser Cys Arg Ser Arg Pro Val Glu Ser Ser Cys Ser
1               5                   10

<210> SEQ ID NO 40
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is an amino acid residue selected from isoleucine and valine
<220> FEATURE:
<221> NAME/KEY: MISC_FEATURE
<222> LOCATION: (5)..(5)
<223> OTHER INFORMATION: Xaa is an amino acid residue selected from histidine and tyrosine
<220> FEATURE:
<221> NAME/KEY: MISC_FEATURE
<222> LOCATION: (6)..(6)
<223> OTHER INFORMATION: Xaa is an amino acid residue selected from aspartic acid and asparagine
<220> FEATURE:
<221> NAME/KEY: MISC_FEATURE
<222> LOCATION: (7)..(7)
<223> OTHER INFORMATION: Xaa is an amino acid residue selected from asparagine and serine

<400> SEQUENCE: 40

Cys Arg Ile Xaa Xaa Xaa Xaa Asn Cys
1               5

<210> SEQ ID NO 41
<211> LENGTH: 9
<212> TYPE: PRT
<213> ORGANISM: Homo sapiens

<400> SEQUENCE: 41

Cys Arg Ile Ile His Asn Asn Asn Cys
1               5

<210> SEQ ID NO 42
<211> LENGTH: 10
<212> TYPE: PRT

<213> ORGANISM: Homo sapiens

<400> SEQUENCE: 42

Cys Arg Ile Ile His Asn Asn Asn Cys Gly
1               5                   10

<210> SEQ ID NO 43
<211> LENGTH: 9
<212> TYPE: PRT
<213> ORGANISM: Homo sapiens

<400> SEQUENCE: 43

Cys Arg Ile Val Tyr Asp Ser Asn Cys
1               5

<210> SEQ ID NO 44
<211> LENGTH: 10
<212> TYPE: PRT
<213> ORGANISM: Homo sapiens

<400> SEQUENCE: 44

Cys Arg Ile Val Tyr Asp Ser Asn Cys Gly
1               5                   10

<210> SEQ ID NO 45
<211> LENGTH: 6
<212> TYPE: PRT
<213> ORGANISM: Homo sapiens

<400> SEQUENCE: 45

Tyr Leu Arg Ile Val Gln
1               5

<210> SEQ ID NO 46
<211> LENGTH: 5
<212> TYPE: PRT
<213> ORGANISM: Homo sapiens

<400> SEQUENCE: 46

Leu Arg Ile Val Gln
1               5

<210> SEQ ID NO 47
<211> LENGTH: 4
<212> TYPE: PRT
<213> ORGANISM: Homo sapiens

<400> SEQUENCE: 47

Arg Ile Val Gln
1

<210> SEQ ID NO 48
<211> LENGTH: 6
<212> TYPE: PRT
<213> ORGANISM: Canis lupus familiaris

<400> SEQUENCE: 48

Tyr Leu Arg Val Met Lys
1               5

<210> SEQ ID NO 49
<211> LENGTH: 5
<212> TYPE: PRT
<213> ORGANISM: Canis lupus familiaris -continued

```
<400> SEQUENCE: 49

Leu Arg Val Met Lys
1               5


<210> SEQ ID NO 50
<211> LENGTH: 4
<212> TYPE: PRT
<213> ORGANISM: Canis lupus familiaris

<400> SEQUENCE: 50

Arg Val Met Lys
1


<210> SEQ ID NO 51
<211> LENGTH: 6
<212> TYPE: PRT
<213> ORGANISM: Homo sapiens

<400> SEQUENCE: 51

Tyr Leu Lys Leu Leu Lys
1               5


<210> SEQ ID NO 52
<211> LENGTH: 5
<212> TYPE: PRT
<213> ORGANISM: Homo sapiens

<400> SEQUENCE: 52

Leu Lys Leu Leu Lys
1               5


<210> SEQ ID NO 53
<211> LENGTH: 4
<212> TYPE: PRT
<213> ORGANISM: Homo sapiens

<400> SEQUENCE: 53

Lys Leu Leu Lys
1
```

COMPOSITIONS FOR TREATING RESPIRATORY TRACT INFECTION AND USES THEREOF

CROSS-REFERENCE TO RELATED APPLICATIONS

The present application is the U.S. national stage of International Application PCT/AU2021/050229, filed Mar. 16, 2021, which claims priority to Australian Patent Application No. 2020904226, filed Nov. 16, 2020; Australian Patent Application No. 2020900818, filed Mar. 17, 2020, and Australian Patent Application No. 2020900807, filed Mar. 16, 2020.

SEQUENCE LISTING

The present application contains a Sequence Listing which is being submitted electronically in TXT file format and is hereby incorporated by reference in its entirety. Said TXT copy is named 017227-0264 Sequence Listing 35582506.txt and is 9,617 bytes in size.

FIELD OF THE INVENTION

The invention relates generally to cyclic peptides suitable for treating respiratory tract infection and uses thereof.

BACKGROUND

All references, including any patent or patent application cited in this specification are hereby incorporated by reference to enable full understanding of the invention. Nevertheless, such references are not to be read as constituting an admission that any of these documents forms part of the common general knowledge in the art, in Australia or in any other country.

Respiratory tract infections by pathogens such as bacteria and viruses remain a major global health problem with significant socioeconomic costs. Whilst treatment of bacterial infections of the respiratory tract largely relies on antibiotics, the standard approach to viral infection remains supportive care and placating symptoms. Whilst such treatments have shown some efficacy, emerging and re-emerging pathogens continue to plague humans and non-human populations, attributed at least in part to mutations that give rise to new strains with enhanced infectivity and/or resistance to existing pharmacological intervention. The lack of timely available antiviral agents, including vaccines, has also made it difficult to contain viral outbreaks globally.

There are over 200 known serological strains of virus that cause respiratory tract infection, the most common of which include rhinoviruses (30-50%). Others include coronaviruses (10-15%), influenza (5-15%), human parainfluenza viruses, human respiratory syncytial virus, adenoviruses, enteroviruses, and metapneumovirus. While over 30 coronaviruses have been identified, only 3 or 4 are known to cause respiratory tract infection in humans. Moreover, coronaviruses are typically difficult to culture in vitro, making it difficult to study their function and develop suitable therapies. Coronaviruses are enveloped, positive-stranded RNA viruses that bud from the endoplasmic reticulum-Golgi intermediate compartment or the cis-Golgi network. Coronaviruses infect humans and animals. The human coronaviruses, 229E, OC43 and the more recently identified severe acute respiratory syndrome coronavirus 2 (SARS-CoV-2; see Zhu N et al., 2019. *N Engl J Med.* 2020), are known to be the major causes of respiratory tract infection and can cause pneumonia, in particular in older adults, neonates and immunocompromised individuals. Illustrative examples of coronaviruses that lead to respiratory tract infection are described in US patent publication no. 20190389816, the contents of which are incorporated herein by reference in their entirety.

Another pervasive viral infection is caused by human rhinovirus (HRV), which is a member of the Enterovirus genus in the Picornaviridae family. HRV can infect the upper and lower respiratory tract, including the nasal mucosa, sinuses and middle ear, with infections producing symptoms of the common cold. Infections are typically self-limiting and restricted to the upper airways.

Some viral infections are also asymptomatic in one person but infectious in another. In these cases, transmission of the virus can be widespread as the infected person does not appear ill. Transmission is particularly detrimental in schools, hospitals, nursing homes and others with susceptible populations living in close quarters.

There are currently very few approved antiviral agents for the treatment or prevention of viral infections of the respiratory tract, including the flu or the common cold. These include oseltamivir phosphate (trade name Tamiflu®), zanamivir (trade name Relenza®), peramivir (trade name Rapivab®) and baloxavir marboxil (trade name Xofluza®). Treatment of respiratory tract infections are typically based on management of symptoms (e.g., sneezing, nasal congestion, rhinorrhea, eye irritation, sore throat, cough, headaches, fever, chills), typically with over the counter oral antihistamines, aspirin, cough suppressants, and nasal decongestants. Symptomatic treatment usually involves taking anti-histamines and/or vasoconstrictive decongestants, many of which have undesirable side-effects such a drowsiness.

Hence, there is an urgent need for broad-spectrum treatment strategies effective for alleviating respiratory tract infection by pathogens such as bacteria and viruses with limited or minimal side effects. The present invention solves, or at least partly alleviates this problem by providing compositions that are effective at treating respiratory tract infection, including viral infection.

SUMMARY OF THE INVENTION

In an aspect disclosed herein, there is provided a method of treating a respiratory tract infection in a subject, the method comprising administering to a subject in need thereof a therapeutically effective amount of a peptide of formula (I), or a pharmaceutically acceptable salt thereof:

(I) (SEQ ID NO: 1)

$R^1$-CRSVEGSCG-$R^2$ wherein

- $R^1$ is selected from the group consisting of YLRIVQ (SEQ ID NO:45), LRIVQ (SEQ ID NO:46), RIVQ (SEQ ID NO:47), IVQ, VQ, and Q, or $R^1$ is absent; and
- $R^2$ is F (phenylalanine), or $R^2$ is absent.

In an embodiment, the peptide is selected from the group consisting of (SEQ ID NO: 2)

YLRIVQCRSVEGSCGF,

-continued

```
(SEQ ID NO: 3)
LRIVQCRSVEGSCGF,

(SEQ ID NO: 4)
CRSVEGSCG
and

(SEQ ID NO: 5)
CRSVEGSCGF.
```

In another aspect disclosed herein, there is provided a pharmaceutical composition comprising a peptide of formula (I), or a pharmaceutically acceptable salt thereof, for use in the treatment of a respiratory tract infection in a subject:

(I) (SEQ ID NO: 1)

$R^1$-CRSVEGSCG-$R^2$ wherein $R^1$ is selected from the group consisting of YLRIVQ (SEQ ID NO:45), LRIVQ (SEQ ID NO:46), RIVQ (SEQ ID NO:47), IVQ, VQ, and Q, or $R^1$ is absent; and $R^2$ is F (phenylalanine), or $R^2$ is absent.

In another aspect disclosed herein, there is provided use of a peptide of formula (I), or a pharmaceutically acceptable salt thereof, in the manufacture of a medicament for the treatment of a respiratory tract infection in a subject:

(I) (SEQ ID NO: 1)

$R^1$-CRSVEGSCG-$R^2$ wherein $R^1$ is selected from the group consisting of YLRIVQ (SEQ ID NO:45), LRIVQ (SEQ ID NO:46), RIVQ (SEQ ID NO:47), IVQ, VQ, and Q, or $R^1$ is absent; and $R^2$ is F (phenylalanine), or $R^2$ is absent.

In another aspect disclosed herein, there is provided a method of treating a respiratory tract infection in a subject, the method comprising administering to a subject a therapeutically effective amount of a peptide of formula (II), or a pharmaceutically acceptable salt thereof:

(II) (SEQ ID NO: 6)

$R^1$-CRRFVESSC-$R^2$ wherein $R^1$ is selected from the group consisting of YLRVMK (SEQ ID NO:48), LRVMK (SEQ ID NO:49), RVMK (SEQ ID NO:50), VMK, MK, and K, or $R^1$ is absent; and $R^2$ is selected from the group consisting of A (alanine) and AF (alanine-phenylalanine), or $R^2$ is absent.

In another aspect disclosed herein, there is provided a pharmaceutical composition comprising a peptide of formula (II), or a pharmaceutically acceptable salt thereof, for use in the treatment of a respiratory tract infection in a subject:

(II) (SEQ ID NO: 6)

$R^1$-CRRFVESSC-$R^2$ wherein $R^1$ is selected from the group consisting of YLRVMK (SEQ ID NO:48), LRVMK (SEQ ID NO:49), RVMK (SEQ ID NO:50), VMK, MK, and K, or $R^1$ is absent; and $R^2$ is selected from the group consisting of A (alanine) and AF (alanine-phenylalanine), or $R^2$ is absent.

In another aspect disclosed herein, there is provided a use of a peptide of formula (II), or a pharmaceutically acceptable salt thereof, in the manufacture of a medicament for the treatment of a respiratory tract infection in a subject:

(II) (SEQ ID NO: 6)

$R^1$-CRRFVESSC-$R^2$ wherein $R^1$ is selected from the group consisting of YLRVMK (SEQ ID NO:48), LRVMK (SEQ ID NO:49), RVMK (SEQ ID NO:50), VMK, MK, and K, or $R^1$ is absent; and $R^2$ is selected from the group consisting of A (alanine) and AF (alanine-phenylalanine), or $R^2$ is absent.

In an embodiment, the peptide is selected from the group consisting of

```
(SEQ ID NO: 7)
YLRVMKCRRFVESSCAF,

(SEQ ID NO: 8)
LRVMKCRRFVESSCAF,

(SEQ ID NO: 9)
CRRFVESSCAF
and

(SEQ ID NO: 10)
CRRFVESSCA.
```

In another aspect disclosed herein, there is provided a method of treating a respiratory tract infection in a subject, the method comprising administering to a subject in need thereof a therapeutically effective amount of a peptide of formula (III), or a pharmaceutically acceptable salt thereof:

(III) (SEQ ID NO: 11)

$R^1$-C-R-$X^1$-$X^2$-P-$X^3$-$X^4$-$X^5$-$X^6$-C-$R^2$ wherein $X^1$, $X^3$, $X^5$, and $X^6$ is an amino acid residue selected from the group consisting of serine, alanine, valine, leucine, isoleucine and glycine;

$X^2$ is arginine or lysine;

$X^4$ is glutamic acid or aspartic acid;

$R^1$ is selected from the group consisting of:

```
S,

(SEQ ID NO: 12)
HS,

(SEQ ID NO: 13)
GHS,

(SEQ ID NO: 14)
PGHS,

(SEQ ID NO: 15)
```

-continued

APGHS, (SEQ ID NO: 16)
EAPGHS, (SEQ ID NO: 17)
SEAPGHS, (SEQ ID NO: 18)
SSEAPGHS, (SEQ ID NO: 19)
PSSEAPGHS, (SEQ ID NO: 20)
DPSSEAPGHS
and (SEQ ID NO: 21)
IDPSSEAPGHS, or $R^1$ is absent; and $R^2$ is selected from the group consisting of

S, (SEQ ID NO: 22)
SS, (SEQ ID NO: 23)
SSK, (SEQ ID NO: 24)
SSKF, (SEQ ID NO: 25)
SSKFS, (SEQ ID NO: 26)
SSKFSW, (SEQ ID NO: 27)
SSKFSWD, (SEQ ID NO: 28)
SSKFSWDE, (SEQ ID NO: 29)
SSKFSWDEY, (SEQ ID NO: 30)
SSKFSWDEYE, (SEQ ID NO: 31)
SSKFSWDEYEQ, (SEQ ID NO: 32)
SSKFSWDEYEQY, (SEQ ID NO: 33)
SSKFSWDEYEQYK, (SEQ ID NO: 34)
SSKFSWDEYEQYKK,
and (SEQ ID NO: 35)
SSKFSWDEYEQYKKE, or $R^2$ is absent;

or a pharmaceutically acceptable salt thereof.

In another aspect disclosed herein, there is provided a pharmaceutical composition comprising a peptide of formula (III), or a pharmaceutically acceptable salt thereof, for use in the treatment of a respiratory tract infection in a subject:

(III)
(SEQ ID NO: 11)
$R^1$-C-R-$X^1$-$X^2$-P-$X^3$-$X^4$-$X^5$-$X^6$-C-$R^2$ wherein $X^1$, $X^3$, $X^5$, and $X^6$ is an amino acid residue selected from the group consisting of serine, alanine, valine, leucine, isoleucine and glycine;

$X^2$ is arginine or lysine;

$X^4$ is glutamic acid or aspartic acid;

$R^1$ is selected from the group consisting of:

S, (SEQ ID NO: 12)
HS, (SEQ ID NO: 13)
GHS, (SEQ ID NO: 14)
PGHS, (SEQ ID NO: 15)
APGHS, (SEQ ID NO: 16)
EAPGHS, (SEQ ID NO: 17)
SEAPGHS, (SEQ ID NO: 18)
SSEAPGHS, (SEQ ID NO: 19)
PSSEAPGHS, (SEQ ID NO: 20)
DPSSEAPGHS
and (SEQ ID NO: 21)
IDPSSEAPGHS, or $R^1$ is absent; and $R^2$ is selected from the group consisting of

S, (SEQ ID NO: 22)
SS, (SEQ ID NO: 23)
SSK, (SEQ ID NO: 24)
SSKF, (SEQ ID NO: 25)
SSKFS, (SEQ ID NO: 26)
SSKFSW, (SEQ ID NO: 27)
SSKFSWD, (SEQ ID NO: 28)

-continued

SSKFSWDE, (SEQ ID NO: 29)
SSKFSWDEY, (SEQ ID NO: 30)
SSKFSWDEYE, (SEQ ID NO: 31)
SSKFSWDEYEQ, (SEQ ID NO: 32)
SSKFSWDEYEQY, (SEQ ID NO: 33)
SSKFSWDEYEQYK, (SEQ ID NO: 34)
SSKFSWDEYEQYKK,
and (SEQ ID NO: 35)
SSKFSWDEYEQYKKE, or $R^2$ is absent.

In another aspect disclosed herein, there is provided a use of a peptide of formula (III), or a pharmaceutically acceptable salt thereof, in the manufacture of a medicament for the treatment of a respiratory tract infection in a subject:

(III)

(SEQ ID NO: 11)
$R^1$-C-R-$X^1$-$X^2$-P-$X^3$-$X^4$-$X^5$-$X^6$-C-$R^2$ wherein $X^1$, $X^3$, $X^5$, and $X^6$ is an amino acid residue selected from the group consisting of serine, alanine, valine, leucine, isoleucine and glycine;

$X^2$ is arginine or lysine;

$X^4$ is glutamic acid or aspartic acid;

$R^1$ is selected from the group consisting of:

S, (SEQ ID NO: 12)
HS, (SEQ ID NO: 13)
GHS, (SEQ ID NO: 14)
PGHS, (SEQ ID NO: 15)
APGHS, (SEQ ID NO: 16)
EAPGHS, (SEQ ID NO: 17)
SEAPGHS, (SEQ ID NO: 18)
SSEAPGHS, (SEQ ID NO: 19)
PSSEAPGHS, (SEQ ID NO: 20)
DPSSEAPGHS
and (SEQ ID NO: 21)
IDPSSEAPGHS, or $R^1$ is absent; and $R^2$ is selected from the group consisting of

S, (SEQ ID NO: 22)
SS, (SEQ ID NO: 23)
SSK, (SEQ ID NO: 24)
SSKF, (SEQ ID NO: 25)
SSKFS, (SEQ ID NO: 26)
SSKFSW, (SEQ ID NO: 27)
SSKFSWD, (SEQ ID NO: 28)
SSKFSWDE, (SEQ ID NO: 29)
SSKFSWDEY, (SEQ ID NO: 30)
SSKFSWDEYE, (SEQ ID NO: 31)
SSKFSWDEYEQ, (SEQ ID NO: 32)
SSKFSWDEYEQY, (SEQ ID NO: 33)
SSKFSWDEYEQYK, (SEQ ID NO: 34)
SSKFSWDEYEQYKK,
and (SEQ ID NO: 35)
SSKFSWDEYEQYKKE, or $R^2$ is absent.

In another aspect disclosed herein, there is provided a method of treating a respiratory tract infection in a subject, the method comprising administering to a subject in need thereof a therapeutically effective amount of a peptide of formula (IV) or a pharmaceutically acceptable salt thereof:

(IV)

(SEQ ID NO: 40)
$R^1$-C-R-I-$X^1$-$X^2$-$X^3$-$X^4$-N-C-$R^2$ wherein $X_1$ is an amino acid residue selected from isoleucine (I) and valine (V);

$X_2$ is an amino acid residue selected from histidine (H) and tyrosine (Y);

$X_3$ is an amino acid residue selected from aspartic acid (D) and asparagine (N);

$X_4$ is an amino acid residue selected from asparagine (N) and serine (S);

$R^1$ is selected from the group consisting of YLKLLK (SEQ ID NO:51), LKLLK (SEQ ID NO:52), KLLK (SEQ ID NO:53), LLK, LL, K or $R^1$ is absent; and $R^2$ is G (glycine), or $R^2$ is absent, or $R^2$ is a pharmaceutically acceptable carrier.

In another aspect disclosed herein, there is provided a pharmaceutical composition comprising a peptide of formula (IV) or a pharmaceutically acceptable salt thereof, for use in the treatment of a respiratory tract infection in a subject:

```
(IV)
                                        (SEQ ID NO: 40)
R1-C-R-I-X1-X2-X3-X4-N-C-R2
```

wherein $X_1$ is an amino acid residue selected from isoleucine (I) and valine (V);

$X_2$ is an amino acid residue selected from histidine (H) and tyrosine (Y);

$X_3$ is an amino acid residue selected from aspartic acid (D) and asparagine (N);

$X_4$ is an amino acid residue selected from asparagine (N) and serine (S);

$R^1$ is selected from the group consisting of YLKLLK (SEQ ID NO:51), LKLLK (SEQ ID NO:52), KLLK (SEQ ID NO:53), LLK, LL, K or $R^1$ is absent; and $R^2$ is G (glycine), or $R^2$ is absent, or $R^2$ is a pharmaceutically acceptable carrier.

In another aspect disclosed herein, there is provided a use of a peptide of formula (IV) or a pharmaceutically acceptable salt thereof, in the manufacture of a medicament for the treatment of a respiratory tract infection in a subject:

```
(IV)
                                        (SEQ ID NO: 40)
R1-C-R-I-X1-X2-X3-X4-N-C-R2
```

wherein $X_1$ is an amino acid residue selected from isoleucine (I) and valine (V);

$X_2$ is an amino acid residue selected from histidine (H) and tyrosine (Y);

$X_3$ is an amino acid residue selected from aspartic acid (D) and asparagine (N);

$X_4$ is an amino acid residue selected from asparagine (N) and serine (S);

$R^1$ is selected from the group consisting of YLKLLK (SEQ ID NO:51), LKLLK (SEQ ID NO:52), KLLK (SEQ ID NO:53), LLK, LL, K or $R^1$ is absent; and $R^2$ is G (glycine), or $R^2$ is absent, or $R^2$ is a pharmaceutically acceptable carrier.

In an embodiment, the peptide of formula (IV) is selected from the group consisting of amino acid sequence CRIIHNNNC (SEQ ID NO:41), CRIIHNNNCG (SEQ ID NO:42), CRIVYDSNC (SEQ ID NO:43) and CRIVYDSNCG (SEQ ID NO:44).

DETAILED DESCRIPTION OF THE INVENTION

Figure 1:
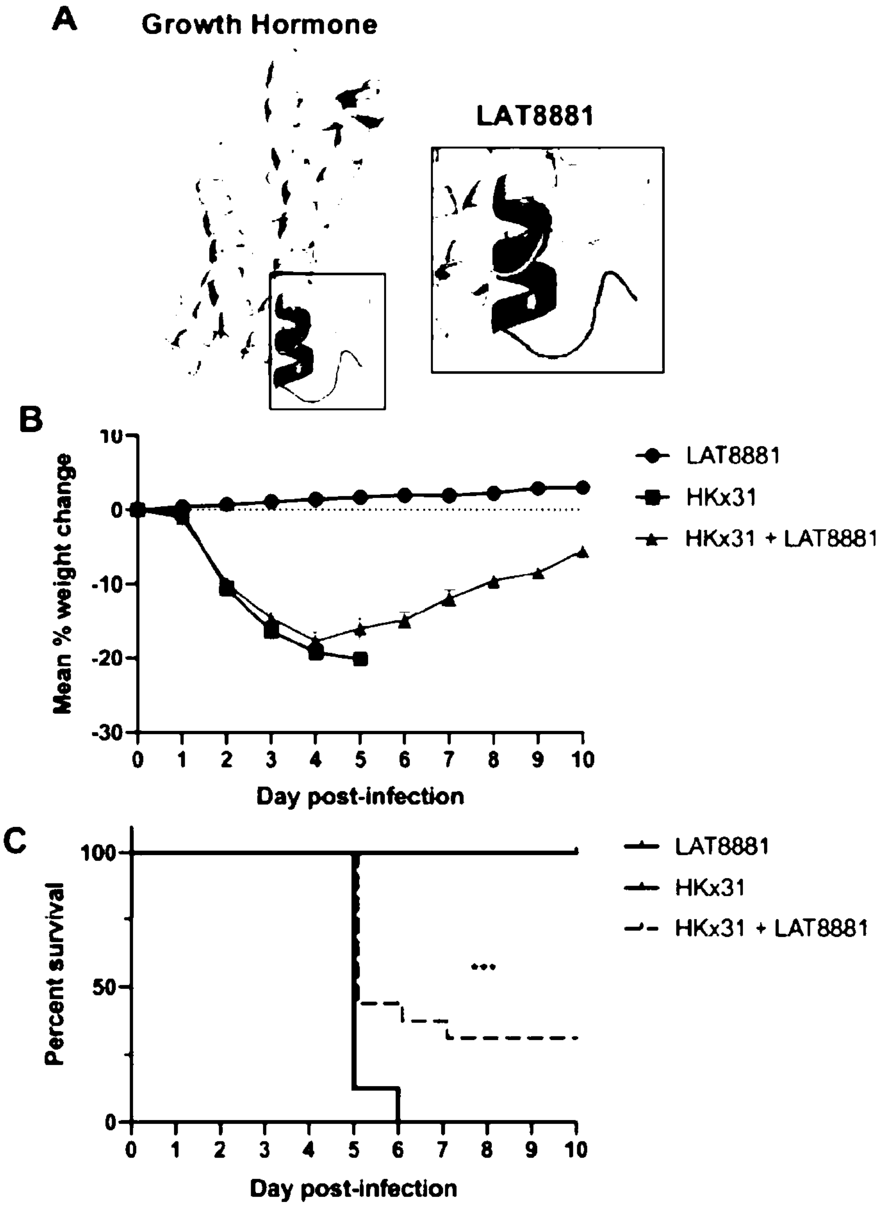
FIG. 1 shows that prophylactic and recurrent LAT8881 treatment during severe IAV infection improves survival. (A) Schematic of Growth Hormone structure (green, http://www.rcsb.org/structure/1HGU). The synthetic compound LAT8881 comprises the short C-terminal region (red) and is cyclised by a disulphide bond between two cysteine residues as shown. (B, C) Groups of 16 C57BL/6 mice were treated with LAT8881 (20 mg/kg) via the intranasal route 24 hours prior to intranasal infection with 105 PFU of HKx31 IAV. Mice received additional LAT8881 treatments every 48 hours following the initial treatment. Uninfected control mice received LAT8881 alone and IAV-infected control mice received PBS alone. (B) Mouse weights were recorded daily and results are expressed as mean percent weight change ±SEM. (C) Survival curves are shown. ***p<0.001 HKx31 vs HKx31+LAT8881, Mantel-Cox log-rank test.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

As used herein, the term "about" refers to a quantity, level, value, dimension, size, or amount that varies by as much as 10% (e.g, by 10%, 9%, 8%, 7%, 6%, 5%, 4%, 3%, 2% or 1%) to a reference quantity, level, value, dimension, size, or amount.

Throughout this specification, unless the context requires otherwise, the words "comprise", "comprises" and "comprising" will be understood to imply the inclusion of a stated step or element or group of steps or elements but not the exclusion of any other step or element or group of steps or elements.

Peptides of Formula (I)

The present inventor has surprisingly found that peptides of formula (I) (SEQ ID NO:1) can alleviate at least some of the symptoms of a respiratory tract infection. The present inventor has also surprisingly found that peptides of formula (I) are effective at limiting viral replication in vivo and reducing hyper-inflammation and severe disease during IAV infection. Thus, in an aspect disclosed herein, there is provided a method of treating a respiratory tract infection in a subject, the method comprising administering to a subject in need thereof a therapeutically effective amount of a peptide of formula (I), or a pharmaceutically acceptable salt thereof:

(I)
(SEQ ID NO: 1)
$R^1$-CRSVEGSCG-$R^2$ wherein $R^1$ is selected from the group consisting of YLRIVQ (SEQ ID NO:45), LRIVQ (SEQ ID NO:46), RIVQ (SEQ ID NO:47), IVQ, VQ, and Q, or $R^1$ is absent; and $R^2$ is F (phenylalanine), or $R^2$ is absent.

In a preferred embodiment, the peptide is YLRIVQCRSVEGSCGF (SEQ ID NO:2). SEQ ID NO:2 (also referred to as AOD9604) is the C-terminal fragment of human growth hormone (hGH) spanning amino acid residues 178-192 of hGH (see, e.g., GenBank Accession numbers AAA72260.1, AML27053.1 and ADE06645.1), with an additional tyrosine residue at the N-terminus of the peptide.

In an embodiment disclosed herein, le is absent. In another embodiment, $R^2$ is absent. In yet another embodiment, $R^1$ and $R^2$ are absent.

In an embodiment disclosed herein, the peptide of formula (I) is from 9 to 16 amino acid residues in length, preferably 9, 10, 11, 12, 13, 14, 15 or 16 amino acid residues in length. The peptide of formula (I) will typically comprise a disulphide bond between the two cysteine (C) residues, thereby forming a cyclic peptide between the two cysteine residues.

In an embodiment, the peptide of formula (I) is selected from the group consisting of YLRIVQCRSVEGSCGF (SEQ ID NO:2), LRIVQCRSVEGSCGF (SEQ ID NO:3), CRSVEGSCG (SEQ ID NO:4) and CRSVEGSCGF (SEQ ID NO:5).

In a preferred embodiment, the peptide of formula (I) is CRSVEGSCG (SEQ ID NO:4). In another preferred embodiment, the peptide of formula (I) is CRSVEGSCGF (SEQ ID NO:5).

Peptides of Formula (II)

The present disclosure also extends to non-human variants of the peptides of formula (I) that have therapeutic properties for treating respiratory tract infection as their human counterparts. Suitable non-human variants of the peptides of formula (I) will be familiar to persons skilled in the art, illustrative examples of which are disclosed in WO 2013/082667, the contents of which is incorporated herein by reference. Thus, in an aspect disclosed herein, there is provided a method of treating a respiratory tract infection in a subject, the method comprising administering to a subject in need thereof a therapeutically effective amount of a peptide of formula (II), or a pharmaceutically acceptable salt thereof:

(II)
(SEQ ID NO: 6)
$R^1$-CRRFVESSC-$R^2$ wherein $R^1$ is selected from the group consisting of YLRVMK (SEQ ID NO:48), LRVMK (SEQ ID NO:49), RVMK (SEQ ID NO:50), VMK, MK, and K, or $R^1$ is absent; and $R^2$ is selected from the group consisting of A (alanine) and AF (alanine-phenylalanine), or $R^2$ is absent. The peptide of formula (II) is representative of a non-human variant of formula (I), as is found, for example in canine, equine and feline subjects.

In an embodiment, the peptide of formula (II) is selected from the group consisting of YLRVMKCRRFVESSCAF (SEQ ID NO:7), LRVMKCRRFVESSCAF (SEQ ID NO:8), CRRFVESSCAF (SEQ ID NO:9) and CRRFVESSCA (SEQ ID NO:10).

The peptide of formula (II) is from 9 to 17 amino acid residues in length, preferably 9, 10, 11, 12, 13, 14, 15, 16 or 17 amino acid residues in length. The peptide of formula (II) will typically comprise a disulphide bond between the two cysteine (C) residues, thereby forming a cyclic peptide between the two cysteine residues. In an embodiment, the peptide of formula (II) is selected from the group consisting of YLRVMKCRRFVESSCAF (SEQ ID NO:7), LRVMKCRRFVESSCAF (SEQ ID NO:8), CRRFVESSCAF (SEQ ID NO:9) and CRRFVESSCA (SEQ ID NO:10). In an embodiment, the peptide is YLRVMKCRRFVESSCAF (SEQ ID NO:7). In another embodiment, the peptide is CRRFVESSCAF (SEQ ID NO:9). In another embodiment, the peptide is CRRFVESSCA (SEQ ID NO:10).

Peptides of Formula (III)

The present disclosure also extends to peptides of formula (III) as having therapeutic properties for the treatment of respiratory tract infection. Thus, in another aspect disclosed herein, there is provided a method of treating a respiratory tract infection in a subject, the method comprising administering to a subject in need thereof a therapeutically effective amount of a peptide of formula (III):

```
(III)
                              (SEQ ID NO: 11)
R1-C-R-X1-X2-P-X3-X4-X5-X6-C-R2
```

$R^1$-C-R-$X^1$-$X^2$-P-$X^3$-$X^4$-$X^5$-$X^6$-C-$R^2$ wherein $X^1$, $X^3$, $X^5$, and $X^6$ is an amino acid residue selected from the group consisting of serine, alanine, valine, leucine, isoleucine and glycine;

$X^2$ is arginine or lysine;

$X^4$ is glutamic acid or aspartic acid;

$R^1$ is selected from the group consisting of:

```
S,

            (SEQ ID NO: 12)
HS,

            (SEQ ID NO: 13)
GHS,

            (SEQ ID NO: 14)
PGHS,

            (SEQ ID NO: 15)
APGHS,

            (SEQ ID NO: 16)
EAPGHS,

            (SEQ ID NO: 17)
SEAPGHS,

            (SEQ ID NO: 18)
SSEAPGHS,

            (SEQ ID NO: 19)
PSSEAPGHS,

            (SEQ ID NO: 20)
DPSSEAPGHS,
and

            (SEQ ID NO: 21)
IDPSSEAPGHS,
```

or $R^1$ is absent; and $R^2$ is selected from the group consisting of

```
S,

            (SEQ ID NO: 22)
SS,

            (SEQ ID NO: 23)
SSK,

            (SEQ ID NO: 24)
SSKF,

            (SEQ ID NO: 25)
SSKFS,

            (SEQ ID NO: 26)
SSKFSW,

            (SEQ ID NO: 27)
SSKFSWD,

            (SEQ ID NO: 28)
SSKFSWDE,

            (SEQ ID NO: 29)
SSKFSWDEY,
```

-continued

```
            (SEQ ID NO: 30)
SSKFSWDEYE,

            (SEQ ID NO: 31)
SSKFSWDEYEQ,

            (SEQ ID NO: 32)
SSKFSWDEYEQY,

            (SEQ ID NO: 33)
SSKFSWDEYEQYK,

            (SEQ ID NO: 34)
SSKFSWDEYEQYKK,
and

            (SEQ ID NO: 35)
SSKFSWDEYEQYKKE,
```

or $R^2$ is absent.

In an embodiment, one or both of $R^1$ and $R^2$ further comprises polyethylene glycol (PEG). The PEG may have a molecular weight in the range of 220 to 5500 Da, preferably 220 to 2500 Da, or more preferably 570 to 1100 Da.

In an embodiment, $R^1$ is absent. In another embodiment, $R^2$ is absent. In yet another embodiment, $R^1$ and $R^2$ are absent.

In an embodiment, $R^1$ is capped with an N-terminal capping group. The term "N-terminal capping group" typically refers to a group that blocks the reactivity of the N-terminal amino group. Suitable N-terminal capping groups will be familiar to persons skilled in the art, illustrative examples of which include acyl groups that form amide groups with the N-terminal amino group, for example, the N-terminal capping group forms a —NHC(O)Ra, where the NH is from the N-terminal amino group and Ra is alkyl, alkenyl, alkynyl, cycloalkyl or aryl. In an embodiment, the N-terminal capping group is —$C(O)CH_3$ (acyl), forming —$NHC(O)CH_3$.

In an embodiment, $R^1$ is a serine residue (S).

In another embodiment, $R^2$ is capped with an C-terminal capping group. The term "C-terminal capping group" typically refers to a group that blocks the reactivity of the C-terminal carboxylic acid. Suitable C-terminal capping groups form amide groups or esters with the C-terminal carboxylic acid, for example, the C-terminal capping group forms a —$C(O)NHR^a$ or —C(O)OR, $^b$ where the C(O) is from the C-terminal carboxylic acid group and $R^a$ is hydrogen, alkyl, alkenyl, alkynyl, cycloalkyl or aryl and $R^b$ is alkyl, alkenyl, alkynyl, cycloalkyl or aryl. In particular embodiments, the C-terminal capping group is —$NH_2$, forming —$C(O)NH_2$.

In an embodiment, $R^2$ is a serine residue (S).

In another embodiment, $R^1$ is a serine residue and $R^2$ is a serine residue.

The peptides of formula (III) can be from 10 to 50 amino acid residues in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues in length), preferably 10 to 40 in length, more preferably 10 to 30 in length, more preferably 10 to 25 in length, or more preferably 10 to 20 in length. It is to be understood that a cyclic peptide, as herein described, is one in which the side chains of two amino acid residues (typically cysteine residues) react together to form a covalent bond or in which the C-terminal carboxylic acid and the N-terminal amine group form an amide bond, thereby cyclizing the peptide.

In an embodiment disclosed herein, the peptide of formula (III) has an amino acid sequence selected from the group consisting of:

```
                    (SEQ ID NO: 36)
SCRSRPVESSC;

                    (SEQ ID NO: 37)
CRSRPVESSC;

                    (SEQ ID NO: 38)
CRSRPVESSCS;
and

                    (SEQ ID NO: 39)
SCRSRPVESSCS.
```

Peptides of Formula (IV)

The present disclosure also extends to peptides of formula (IV) as having therapeutic properties for the treatment of respiratory tract infection. Thus, in an aspect disclosed herein, there is provided a method of treating a respiratory tract infection in a subject, the method comprising administering to a subject in need thereof a therapeutically effective amount of a peptide of formula (IV) or a pharmaceutically acceptable salt thereof:

(IV)

(SEQ ID NO: 40)

$R^1$-C-R-I-$X_1$-$X_2$-$X_3$-$X_4$-N-C-$R^2$ wherein $X_1$ is an amino acid residue selected from isoleucine (I) and valine (V);

$X_2$ is an amino acid residue selected from histidine (H) and tyrosine (Y);

$X_3$ is an amino acid residue selected from aspartic acid (D) and asparagine (N);

$X_4$ is an amino acid residue selected from asparagine (N) and serine (S);

$R^1$ is selected from the group consisting of YLKLLK (SEQ ID NO:51), LKLLK (SEQ ID NO:52), KLLK (SEQ ID NO:53), LLK, LL, K or $R^1$ is absent; and $R^2$ is G (glycine), or $R^2$ is absent, or $R^2$ is a pharmaceutically acceptable carrier.

In an embodiment, the peptide of formula (IV) is selected from the group consisting of amino acid sequence CRIIHNNNC (SEQ ID NO:41), CRIIHNNNCG (SEQ ID NO:42), CRIVYDSNC (SEQ ID NO:43) and CRIVYDSNCG (SEQ ID NO:44). In a preferred embodiment, the peptide of formula (IV) is CRIIHNNNC (SEQ ID NO:41). SEQ ID NO:41 (also referred to interchangeably herein as LAT7771) is the C-terminal fragment of human prolactin (PRL) spanning amino acid residues 219-227 of human prolactin precursor (hPRL; see, e.g., NCBI Reference sequence NP_000939.1 and NP_001157030).

The peptides of formulae (I), (II), (III) and (IV) may be made of naturally occurring amino acid residues, proteogenic or non-proteogenic. These amino acids have L-stereochemistry. Naturally occurring amino acids are set out in Table 1, below.

TABLE 1

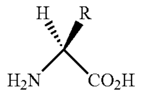

(1)

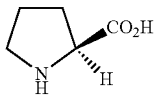

(2)

| Amino Acid | Three-letter Abbreviation | One-letter symbol | Structure of side chain (R) in (1) above |
|---|---|---|---|
| Alanine | Ala | A | $-CH_3$ |
| Arginine | Arg | R | $-(CH_2)_3$ NHC(=N)$NH_2$ |
| Asparagine | Asn | N | $-CH_2CONH_2$ |
| Aspartic acid | Asp | D | $-CH_2CO_2H$ |
| Cysteine | Cys | C | $-CH_2SH$ |
| Glutamine | Gln | Q | $(CH_2)_2CONH_2$ |
| Glutamic acid | Glu | E | $-(CH_2)_2CO_2H$ |
| Glycine | Gly | G | -H |
| Histidine | His | H | $CH_2$(4-imidazoly]) |
| Isoleucine | Ile | I | $-CH(CH_3)CH_2CH_3$ |
| Leucine | Leu | L | $-CH_2CH(CH_3)_2$ |
| Lysine | Lys | K | $-(CH_2)_4NH_2$ |
| Methionine | Met | M | $-(CH_2)_2SCH_3$ |
| Phenylalanine | Phe | F | $-CH_2Ph$ |
| Ornithine | Orn | O | $-(CH_2)_3$ $NH_2$ |
| Proline | Pro | P | see formula (2) above for structure of amino acid |
| Serine | Ser | S | $-CH_2OH$ |
| Threonine | Thr | T | $-CH(CH_3)OH$ |
| Tryptophan | Trp | W | $-CH_2$(3-indolyl) |
| Tyrosine | Tyr | Y | $-CH_2$(4-hydroxyphenyl) |
| Valine | Val | V | $-CH(CH_3)_2$ |

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "cycloalkyl" refers to a saturated and unsaturated (but not aromatic) cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclopentenyl, cyclohexyl, cyclohexenyl, cyclohexadienyl, cycloheptyl and cyclooctyl.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, fluorenyl, phenanthrenyl, biphenyl and binaphthyl.

In an embodiment, a disulphide bond is formed between the two cysteine residues (C) of formulae (I), (II) and (III).

The peptides disclosed herein may be made by methods well known to persons skilled in the art, illustrative examples of which include by solution or solid phase synthesis using Fmoc or Boc protected amino acid residues and recombinant techniques as known in the art using standard microbial culture technology, genetically engineered microbes and recombinant DNA technology (Sambrook and Russell, Molecular Cloning: A Laboratory Manual (3rd Edition), 2001, CSHL Press).

In an embodiment, the peptides of formulae (I), (II), (III) and (IV) are formed as a pharmaceutically acceptable salt. It is to be understood that non-pharmaceutically acceptable salts are also envisaged, since these may be useful as intermediates in the preparation of pharmaceutically acceptable salts or may be useful during storage or transport. Suitable pharmaceutically acceptable salts will be familiar to persons skilled in the art, illustrative examples of which include salts of pharmaceutically acceptable inorganic acids, such as hydrochloric, sulphuric, phosphoric, nitric, carbonic, boric, sulfamic, and hydrobromic acids, or salts of pharmaceutically acceptable organic acids, such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids. Illustrative examples of suitable base salts include those formed with pharmaceutically acceptable cations, such as sodium, potassium, lithium, calcium, magnesium, ammonium and alkylammonium. Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

Also disclosed herein are prodrugs comprising the peptides of formulae (I), (II), (III) or (IV), or the pharmaceutically acceptable salts thereof. As used herein, a "prodrug" typically refers to a compound that can be metabolized in vivo to provide the active peptide of formulae (I), (II), (III) or (IV), or pharmaceutically acceptable salts thereof. In some embodiments, the prodrug itself also shares the same, or substantially the same, therapeutic activity as the peptide of formulae (I), (II), (III) or (IV), or pharmaceutically acceptable salts thereof, as described elsewhere herein.

In some embodiments, the peptides of formulae (I), (II), (III) and (IV), or pharmaceutically acceptable salts thereof, may further comprise a C-terminal capping group. The term "C-terminal capping group", as used herein, refers to a group that blocks the reactivity of the C-terminal carboxylic acid. Suitable C-terminal capping groups form amide groups or esters with the C-terminal carboxylic acid, for example, the C-terminal capping group forms a —C(O)NHR$^a$ or —C(O)OR$^b$ where the C(O) is from the C-terminal carboxylic acid group and R$^a$ is hydrogen, alkyl, alkenyl, alkynyl, cycloalkyl or aryl and R$^b$ is alkyl, alkenyl, alkynyl, cycloalkyl or aryl. In particular embodiments, the C-terminal capping group is —$NH_2$, forming —C(O)$NH_2$. In some embodiments, the peptides of formulae (I) or (II), or pharmaceutically acceptable salts thereof, comprise a C-terminal polyethylene glycol (PEG). In an embodiment, the PEG has a molecular weight in the range of 220 to 5500 Da, preferably 220 to 2500 Da, more preferably 570 to 1100 Da.

In some embodiments, the peptides of formulae (I), (II), (III) and (IV), or pharmaceutically acceptable salts thereof, may further comprise an N-terminal capping group. The term "N-terminal capping group", as used herein, refers to a group that blocks the reactivity of the N-terminal amino group. Suitable N-terminal capping groups are acyl groups that form amide groups with the N-terminal amino group, for example, the N-terminal capping group forms a —NHC(O)R$^a$ where the NH is from the N-terminal amino group and R$^a$ is alkyl, alkenyl, alkynyl, cycloalkyl or aryl. In particular embodiments, the N-terminal capping group is —C(O)$CH_3$ (acyl), forming —NHC(O)$CH_3$.

In some embodiments, the peptides of formulae (I), (II), (III) and (IV), or pharmaceutically acceptable salts thereof, may comprise a C-terminal capping group and an N-terminal capping group, as herein described. It is to be understood that the peptides disclosed herein do not include the full length amino acid sequence of human growth hormone or of a non-human isoform thereof.

The peptides of formulae (I), (II), (III) and (IV), or pharmaceutically acceptable salts thereof, as herein described, can be made be any method known to persons skilled in the art. Illustrative examples of suitable methods include solution or solid phase synthesis using Fmoc or Boc protected amino acid residues, recombinant techniques using microbial culture, genetically engineered microbes, plants and recombinant DNA technology (see, e.g., Sambrook and Russell, Molecular Cloning: A Laboratory Manual (3rd Edition), 2001, CSHL Press).

Methods of Treatment

As described elsewhere herein, the present inventor has surprisingly found, for the first time, that a peptide of formula (I) (SEQ ID NO:1) can alleviate symptoms of respiratory tract infection, including a virus infection. The present inventor has also surprisingly found that peptides of formula (I) are effective at limiting viral replication in vivo and reducing hyper-inflammation and severe disease during IAV infection. The peptides of formula (I) can therefore suitably be used to treat, alleviate or otherwise abrogate the severity of respiratory tract infection in a subject, including one or more symptoms thereof, such as elevated temperature, sweating, chills, cough and wheezing. The present disclosure also extends to the use of formulae (II), (III) and (IV) for treating respiratory tract infection. Thus, the peptides of formulae (I), (II), (III) and (IV), or pharmaceutically acceptable salts thereof, can also suitably be used to treat, alleviate or otherwise abrogate the severity of respiratory tract infection in a subject, including one or more symptoms thereof, such as elevated temperature, sweating, chills, cough and wheezing.

The terms "treating", "treatment" and the like, are used interchangeably herein to mean relieving, reducing, alleviating, ameliorating or otherwise inhibiting the severity of the respiratory tract infection, including one or more symptoms thereof, such as elevated temperature, sweating, chills, cough and wheezing.

The terms "treating", "treatment" and the like also include relieving, reducing, alleviating, ameliorating or otherwise inhibiting the severity of the respiratory tract infection for at least a period of time. It is to be understood that terms "treating", "treatment" and the like do not imply that the respiratory tract infection, or a symptom thereof, is permanently relieved, reduced, alleviated, ameliorated or otherwise inhibited and therefore extend to the temporary relief, reduction, alleviation, amelioration or otherwise inhibition of the severity of the respiratory tract infection, or of one or more symptoms thereof.

The term "subject", as used herein, refers to a mammalian subject for whom treatment of respiratory tract infection is desired. Illustrative examples of suitable subjects include primates, especially humans, companion animals such as cats and dogs and the like, working animals such as horses, donkeys and the like, livestock animals such as sheep, cows, goats, pigs and the like, laboratory test animals such as rabbits, mice, rats, guinea pigs, hamsters and the like and captive wild animals such as those in zoos and wildlife parks, deer, dingoes and the like. In an embodiment, the subject is a human.

It is to be understood that a reference to a subject herein does not imply that the subject has a respiratory tract infection, or a symptom thereof, but also includes a subject that is at risk of developing a respiratory tract infection, or a symptom thereof.

In an embodiment, the methods disclosed herein comprise administering a peptide of formula (I), (II), (III) or (IV), or a pharmaceutically acceptable salt thereof, to a human subject.

The peptides of formula (I), (II), (III) and (IV), or pharmaceutically acceptable salts thereof, are to be administered in a therapeutically effective amount. The phrase "therapeutically effective amount" typically means an amount necessary to attain the desired response. It would be understood by persons skilled in the art that the therapeutically effective amount of peptide will vary depending upon several factors, illustrative examples of which include the health and physical condition of the subject to be treated, the taxonomic group of subject to be treated, the severity of the respiratory tract infection to be treated, the formulation of the composition comprising a peptide of formula (I), (II), (III) or (IV), or a pharmaceutically acceptable salt thereof, the route of administration, and combinations of any of the foregoing.

The therapeutically effective amount will typically fall within a relatively broad range that can be determined through routine trials by persons skilled in the art. Illustrative examples of a suitable therapeutically effective amount of the peptides of formula (I), (II), (III) and (IV), and pharmaceutically acceptable salts thereof, for administration to a human subject include from about 0.001 mg per kg of body weight to about 1 g per kg of body weight, preferably from about 0.001 mg per kg of body weight to about 50 g per kg of body weight, more preferably from about 0.01 mg per kg of body weight to about 1.0 mg per kg of body weight. In an embodiment disclosed herein, the therapeutically effective amount of the peptide of formulae (I), (II), (III) and/or (IV), and/or pharmaceutically acceptable salts thereof, is from about 0.001 mg per kg of body weight to about 1 g per kg of body weight per dose (e.g., 0.001 mg/kg, 0.005 mg/kg, 0.01 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg, 19.5 mg/kg, 20 mg/kg, 20.5 mg/kg, 21 mg/kg, 21.5 mg/kg, 22 mg/kg, 22.5 mg/kg, 23 mg/kg, 23.5 mg/kg, 24 mg/kg, 24.5 mg/kg, 25 mg/kg, 25.5 mg/kg, 26 mg/kg, 26.5 mg/kg, 27 mg/kg, 27.5 mg/kg, 28 mg/kg, 28.5 mg/kg, 29 mg/kg, 29.5 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg of body weight, etc). In an embodiment, the therapeutically effective amount of the peptides of formulae (I), (II), (III) or (IV), or the pharmaceutically acceptable salts thereof, is from about 0.001 mg to about 50 mg per kg of body weight. In an embodiment, the therapeutically effective amount of the peptide of formula (I), (II), (III) or (IV), and pharmaceutically acceptable salts thereof, is from about 0.01 mg to about 100 mg per kg of body weight. In an embodiment, the therapeutically effective amount of the peptide of formula (I), (II), (III) or (IV), or pharmaceutically acceptable salts thereof, is from about 0.1 mg to about 10 mg per kg of body weight, preferably from about 0.1 mg to about 5 mg per kg of body weight, more preferably from about 0.1 mg to about 1.0 mg per kg of body weight. Dosage regimes may be adjusted to provide the optimum therapeutic response. For example, several divided doses may be administered daily, weekly, monthly or other suitable time intervals, or the dose may be proportionally reduced as indicated by the exigencies of the situation.

As noted elsewhere herein, the present inventor has surprisingly found that the peptides described herein are capable of alleviating symptoms of a respiratory tract infection and are effective at limiting viral replication in vivo and reducing hyper-inflammation and severe disease during IAV infection. Thus, in an embodiment disclosed herein, a peptide of formula (I), or a pharmaceutically acceptable salt thereof, is administered to the subject at a therapeutically effective amount that treats a respiratory tract infection in the subject. Therapeutic activity in treating a respiratory tract infection is also ascribed to the peptides of formulae (II), (III) and (IV). Thus, in an embodiment disclosed herein, a peptide of formula (II), (III) or (IV), or pharmaceutically acceptable salts thereof, is administered to the subject at a therapeutically effective amount that treats a respiratory tract infection in the subject.

In an embodiment disclosed herein, the peptides described herein comprise the amino acid sequence CRSVEGSCG (SEQ ID NO:4) or CRSVEGSCGF (SEQ ID NO:5).

Respiratory Tract Infection

Respiratory tract infection (RTI) is typically defined as any infectious disease of the upper or lower respiratory tract. Upper respiratory tract infections (URTIs) include the common cold, laryngitis, pharyngitis/tonsillitis, acute rhinitis, acute rhinosinusitis and acute otitis media. Lower respiratory tract infections (LRTIs) include acute bronchitis, bronchiolitis, pneumonia and tracheitis. Antibiotics are commonly prescribed for RTIs in adults and children in primary care. RTIs are the reason for 60% of all antibiotic prescribing in general practice, and this constitutes a significant cost to the health system (*NICE Clinical Guidelines, No.* 69; Centre for Clinical Practice at NICE (UK), London: National Institute for Health and Clinical Excellence (UK); 2008).

Pathogens that give rise to infection of the upper and/or lower respiratory tracts in human and non-human subjects will be known to persons skilled in the art, and include bacteria and viruses, illustrative examples of which are described in Charlton et al. (*Clinical Microbiology Reviews;* 2018, 32 (1): e00042-18), Popescu et al. (*Microorganisms.* 2019; 7(11): 521) and Kikkert, M. (*J Innate Immun.* 2020; 12(1): 4-20), the contents of which are incorporated herein by reference in their entirety. In an embodiment, the respiratory tract infection is a virus infection.

Viruses that give rise to infection of the respiratory tract in human and non-human subjects (upper and/or lower respiratory tracts) will be known to persons skilled in the art, illustrative examples of which include a picornavirus, a coronavirus, an influenza virus, a parainfluenza virus, a respiratory syncytial virus, an adenovirus, an enterovirus, and a metapneumovirus. Thus, in an embodiment disclosed herein, the virus is selected from the group consisting of a picornavirus, a coronavirus, an influenza virus, a parainfluenza virus, a respiratory syncytial virus, an adenovirus, an enterovirus, and a metapneumovirus. In an embodiment, the virus is an influenza virus. In another embodiment, the virus is a coronavirus. Illustrative examples of coronaviruses that give rise to respiratory tract infection will be familiar to persons skilled in the art, illustrative examples of which include SARS-CoV-2 as previously described in Zhu N et al., (2019. *N Engl J Med.* 2020) and in US patent publication no. 20190389816, the contents of which are incorporated herein by reference in their entirety. In an embodiment, the virus is SARS-CoV-2.

The methods, compositions and uses thereof, as described herein, may be particularly useful for treating respiratory tract infection in subjects with an underlying medical condition that would otherwise exacerbate the respiratory tract infection. Such underlying conditions will be known to persons skilled in the art, illustrative examples of which include chronic obstructive pulmonary disease, asthma, cystic fibrosis, emphysema and lung cancer. In an embodiment, the subject has a further respiratory condition selected from the group consisting of chronic obstructive pulmonary disease, asthma, cystic fibrosis and lung cancer. In another embodiment, the subject is immunocompromised, whether as a result of treatment (e.g., by chemotherapy, radiotherapy) or otherwise (e.g., by HIV infection).

Viral replication of viruses in humans typically begins 2 to 6 hours after initial contact. In some cases, the patient is infectious for a couple of days before the onset of symptoms. Symptoms usually begin about 2 to 5 days after initial infection. Respiratory tract infection such as the common cold is most infectious during the first two to three days of symptoms. There is currently no known treatment that shortens the duration of a cold, although symptoms usually resolve spontaneously in about 7 to 10 days, with some symptoms possibly lasting for up to three weeks. The virus may still be infectious until symptoms have completely resolved.

Routes of Administration

The peptides of formulae (I), (II), (III) and (IV), and pharmaceutically acceptable salts thereof, may be administered to the subject by any suitable route that allows for delivery of the peptides to the subject at a therapeutically effective amount, as herein described. Suitable routes of administration will be known to persons skilled in the art, illustrative examples of which include enteral routes of administration (e.g., oral and rectal), parenteral routes of administration, typically by injection or microinjection (e.g., intramuscular, subcutaneous, intravenous, epidural, intra-articular, intraperitoneal, intracisternal or intrathecal) and topical (transdermal or transmucosal) routes of administration (e.g., buccal, sublingual, vaginal, intranasal or by inhalation, insufflation or nebulization). The peptides of formulae (I), (II), (III) and (IV), and pharmaceutically acceptable salts thereof, may also suitably be administered to the subject as a controlled release dosage form to provide a controlled release of the active agent(s) over an extended period of time. The term "controlled release" typically means the release of the active agent(s) to provide a constant, or substantially constant, concentration of the active agent in the subject over a period of time (e.g., about eight hours up to about 12 hours, up to about 14 hours, up to about 16 hours, up to about 18 hours, up to about 20 hours, up to a day, up to a week, up to a month, or more than a month). Controlled release of the active agent(s) can begin within a few minutes after administration or after expiration of a delay period (lag time) after administration, as may be required. Suitable controlled release dosage forms will be known to persons skilled in the art, illustrative examples of which are described in Anal, A. K. (2010; *Controlled-Release Dosage Forms*. Pharmaceutical Sciences Encyclopedia. 11:1-46).

Without being bound by theory or by a particular mode of application, it may be desirable to elect a route of administration on the basis of the severity of the respiratory tract infection or one or more symptoms thereof. In an embodiment disclosed herein, the peptides of formulae (I), (II), (III) and (IV), or pharmaceutically acceptable salts thereof, are administered to the subject enterally. In an embodiment disclosed herein, the peptides of formula (I), (II), (III) or (IV), or pharmaceutically acceptable salts thereof, are administered to the subject orally. In an embodiment disclosed herein, the peptides of formula (I), (II), (III) or (IV), or pharmaceutically acceptable salts thereof, are administered to the subject parenterally. In another embodiment disclosed herein, the peptides of formula (I), (II), (III) or (IV), or pharmaceutically acceptable salts thereof, are administered to the subject topically.

As described elsewhere herein, "topical" administration typically means application of the active agents to a surface of the body, such as the skin or mucous membranes, suitably in the form of a cream, lotion, foam, gel, ointment, nasal drop, eye drop, ear drop, transdermal patch, transdermal film (e.g., sublingual film) and the like. Topical administration also encompasses administration via the mucosal membrane of the respiratory tract by inhalation or insufflation. In an embodiment disclosed herein, the topical administration is selected from the group consisting of transdermal and transmucosal administration. In an embodiment, the peptides of formula (I), (II), (III) or (IV), or pharmaceutically acceptable salts thereof, are administered to the subject transdermally. In an embodiment, the peptides of formulae (I), (II), (III) and (IV), and pharmaceutically acceptable salts thereof, are administered to the subject by inhalation, insufflation or nebulization.

In an embodiment, the methods comprise orally administering the peptide of formula (I), or a pharmaceutically acceptable salt thereof, to a human. In another embodiment, the methods comprise orally administering the peptide of formula (I), or pharmaceutically acceptable salts thereof, to a non-human subject. In yet another embodiment, the methods comprise orally administering the peptide of formula (I), or a pharmaceutically acceptable salt thereof, to a non-human subject selected from the group consisting of a feline, a canine and an equine.

In an embodiment, the methods comprise orally administering the peptide of formula (II), or a pharmaceutically acceptable salt thereof, to a human. In another embodiment, the methods comprise orally administering the peptide of formula (II), or a pharmaceutically acceptable salt thereof, to a non-human subject. In yet another embodiment, the methods comprise orally administering the peptide of formula (II), or a pharmaceutically acceptable salt thereof, to a non-human subject selected from the group consisting of a feline, a canine and an equine.

In an embodiment, the methods comprise orally administering the peptide of formula (III), or a pharmaceutically acceptable salt thereof, to a human. In another embodiment, the methods comprise orally administering the peptide of formula (III), or a pharmaceutically acceptable salt thereof, to a non-human subject. In yet another embodiment, the methods comprise orally administering the peptide of formula (III), or a pharmaceutically acceptable salt thereof, to a non-human subject selected from the group consisting of a feline, a canine and an equine.

In an embodiment, the methods comprise orally administering the peptide of formula (IV), or a pharmaceutically acceptable salt thereof, to a human. In another embodiment, the methods comprise orally administering the peptide of formula (IV), or a pharmaceutically acceptable salt thereof, to a non-human subject. In yet another embodiment, the methods comprise orally administering the peptide of formula (IV), or a pharmaceutically acceptable salt thereof, to a non-human subject selected from the group consisting of a feline, a canine and an equine.

In an embodiment, the methods comprise administering the peptide of formula (I), or a pharmaceutically acceptable salt thereof, topically to a human. In another embodiment, the methods comprise administering the peptide of formula (I), or a pharmaceutically acceptable salt thereof, topically to a non-human subject. In yet another embodiment, the methods comprise administering the peptide of formula (I), or a pharmaceutically acceptable salt thereof, topically to a non-human subject selected from the group consisting of a feline, a canine and an equine.

In an embodiment, the methods comprise administering the peptide of formula (II), or a pharmaceutically acceptable salt thereof, topically to a human. In another embodiment, the methods comprise administering the peptide of formula (II), or a pharmaceutically acceptable salt thereof, topically to a non-human subject. In yet another embodiment, the methods comprise administering the peptide of formula (II), or a pharmaceutically acceptable salt thereof, topically to a non-human subject selected from the group consisting of a feline, a canine and an equine.

In an embodiment, the methods comprise administering the peptide of formula (III), or a pharmaceutically acceptable salt thereof, topically to a human. In another embodiment, the methods comprise administering the peptide of formula (III), or a pharmaceutically acceptable salt thereof, topically to a non-human subject. In yet another embodiment, the methods comprise administering the peptide of formula (III), or a pharmaceutically acceptable salt thereof, topically to a non-human subject selected from the group consisting of a feline, a canine and an equine.

In an embodiment, the methods comprise administering the peptide of formula (IV), or a pharmaceutically acceptable salt thereof, topically to a human. In another embodiment, the methods comprise administering the peptide of formula (IV), or a pharmaceutically acceptable salt thereof, topically to a non-human subject. In yet another embodiment, the methods comprise administering the peptide of formula (IV), or a pharmaceutically acceptable salt thereof, topically to a non-human subject selected from the group consisting of a feline, a canine and an equine.

In another embodiment, the methods comprise administering the peptide of SEQ ID NO:2, or a pharmaceutically acceptable salt thereof, orally to a human. In another embodiment, the methods comprise administering the peptide of SEQ ID NO:2, or pharmaceutically acceptable salts thereof, orally to a non-human subject. In yet another embodiment, the methods comprise administering the peptide of SEQ ID NO:2, or pharmaceutically acceptable salts thereof, orally to a non-human subject selected from the group consisting of a feline, a canine and an equine.

In another embodiment, the methods comprise administering the peptide of SEQ ID NO:2, or a pharmaceutically acceptable salt thereof, topically to a human. In another embodiment, the methods comprise administering the peptide of SEQ ID NO:2, or pharmaceutically acceptable salts thereof, topically to a non-human subject. In yet another embodiment, the methods comprise administering the peptide of SEQ ID NO:2, or pharmaceutically acceptable salts thereof, topically to a non-human subject selected from the group consisting of a feline, a canine and an equine.

In another embodiment, the methods comprise administering the peptide of SEQ ID NO:7, or pharmaceutically acceptable salts thereof, orally to a non-human subject. In yet another embodiment, the methods comprise administering the peptide of SEQ ID NO:7, or pharmaceutically acceptable salts thereof, orally to a non-human subject selected from the group consisting of a feline, a canine and an equine.

In another embodiment, the methods comprise administering the peptide of SEQ ID NO:7, or pharmaceutically acceptable salts thereof, topically to a non-human subject. In yet another embodiment, the methods comprise administering the peptide of SEQ ID NO:7, or pharmaceutically acceptable salts thereof, topically to a non-human subject selected from the group consisting of a feline, a canine and an equine.

In another embodiment, the methods comprise administering the peptide of SEQ ID NO:36, or pharmaceutically acceptable salts thereof, orally to a non-human subject. In yet another embodiment, the methods comprise administering the peptide of SEQ ID NO:36, or pharmaceutically acceptable salts thereof, orally to a non-human subject selected from the group consisting of a feline, a canine and an equine.

In another embodiment, the methods comprise administering the peptide of SEQ ID NO:36, or pharmaceutically acceptable salts thereof, topically to a non-human subject. In yet another embodiment, the methods comprise administering the peptide of SEQ ID NO:36, or pharmaceutically acceptable salts thereof, topically to a non-human subject selected from the group consisting of a feline, a canine and an equine.

In another embodiment, the methods comprise administering the peptide of SEQ ID NO:41, or pharmaceutically acceptable salts thereof, orally to a non-human subject. In yet another embodiment, the methods comprise administering the peptide of SEQ ID NO:41, or pharmaceutically acceptable salts thereof, orally to a non-human subject selected from the group consisting of a feline, a canine and an equine.

In another embodiment, the methods comprise administering the peptide of SEQ ID NO:41, or pharmaceutically acceptable salts thereof, topically to a non-human subject. In yet another embodiment, the methods comprise administering the peptide of SEQ ID NO:41, or pharmaceutically acceptable salts thereof, topically to a non-human subject selected from the group consisting of a feline, a canine and an equine.

Illustrative examples of topical administration are described elsewhere herein. In an embodiment, the topical administration is transdermal.

In an embodiment disclosed herein, the peptides of formula (I), (II), (III) or (IV), or pharmaceutically acceptable salts thereof, are administered to the subject as a controlled release dosage form, illustrative examples of which are described elsewhere herein. In an embodiment, the methods comprise administering the peptide of formula (I), or a pharmaceutically acceptable salt thereof, to a human as a controlled release dosage form. In another embodiment, the methods comprise administering the peptide of formula (I), or pharmaceutically acceptable salts thereof, to a non-human subject as a controlled release dosage form. In yet another embodiment, the methods comprise administering the peptide of formula (I), or a pharmaceutically acceptable salt thereof, as a controlled release dosage form to a non-human subject selected from the group consisting of a feline, a canine and an equine.

In another embodiment, the methods comprise administering the peptide of formula (II), or a pharmaceutically acceptable salt thereof, to a human as a controlled release dosage form. In another embodiment, the methods comprise administering the peptide of formula (II), or a pharmaceutically acceptable salt thereof, to a non-human subject as a controlled release dosage form. In yet another embodiment, the methods comprise administering the peptide of formula (II), or a pharmaceutically acceptable salt thereof, as a controlled release dosage form to a non-human subject selected from the group consisting of a feline, a canine and an equine.

In another embodiment, the methods comprise administering the peptide of formula (III), or a pharmaceutically acceptable salt thereof, to a human as a controlled release dosage form. In another embodiment, the methods comprise administering the peptide of formula (III), or a pharmaceutically acceptable salt thereof, to a non-human subject as a controlled release dosage form. In yet another embodiment, the methods comprise administering the peptide of formula (III), or a pharmaceutically acceptable salt thereof, as a controlled release dosage form to a non-human subject selected from the group consisting of a feline, a canine and an equine.

In another embodiment, the methods comprise administering the peptide of formula (IV), or a pharmaceutically acceptable salt thereof, to a human as a controlled release dosage form. In another embodiment, the methods comprise administering the peptide of formula (IV), or a pharmaceutically acceptable salt thereof, to a non-human subject as a controlled release dosage form. In yet another embodiment, the methods comprise administering the peptide of formula (IV), or a pharmaceutically acceptable salt thereof, as a controlled release dosage form to a non-human subject selected from the group consisting of a feline, a canine and an equine.

In another embodiment, the methods comprise administering the peptide of SEQ ID NO:2, or a pharmaceutically acceptable salt thereof, to a human as a controlled release dosage form. In another embodiment, the methods comprise administering the peptide of SEQ ID NO:2, or pharmaceutically acceptable salts thereof, to a non-human subject as a controlled release dosage form. In yet another embodiment, the methods comprise administering the peptide of SEQ ID NO:2, or pharmaceutically acceptable salts thereof, as a controlled release dosage form to a non-human subject selected from the group consisting of a feline, a canine and an equine.

In another embodiment, the methods comprise administering the peptide of SEQ ID NO:7, or pharmaceutically acceptable salts thereof, to a non-human subject as a controlled release dosage form. In yet another embodiment, the methods comprise administering the peptide of SEQ ID NO:7, or pharmaceutically acceptable salts thereof, as a controlled release dosage form to a non-human subject selected from the group consisting of a feline, a canine and an equine. In an embodiment, the controlled release dosage form is administered to the subject parenterally, suitable examples of which are described elsewhere herein.

In another embodiment, the methods comprise administering the peptide of SEQ ID NO:36, or pharmaceutically acceptable salts thereof, to a non-human subject as a controlled release dosage form. In yet another embodiment, the methods comprise administering the peptide of SEQ ID NO:36, or pharmaceutically acceptable salts thereof, as a controlled release dosage form to a non-human subject selected from the group consisting of a feline, a canine and an equine. In an embodiment, the controlled release dosage form is administered to the subject parenterally, suitable examples of which are described elsewhere herein.

In another embodiment, the methods comprise administering the peptide of SEQ ID NO:41, or pharmaceutically acceptable salts thereof, to a non-human subject as a controlled release dosage form. In yet another embodiment, the methods comprise administering the peptide of SEQ ID NO:41, or pharmaceutically acceptable salts thereof, as a controlled release dosage form to a non-human subject selected from the group consisting of a feline, a canine and an equine. In an embodiment, the controlled release dosage form is administered to the subject parenterally, suitable examples of which are described elsewhere herein.

As noted elsewhere herein, several (i.e., multiple) divided doses may be administered daily, weekly, monthly or other suitable time intervals, or the dose may be proportionally reduced as indicated by the exigencies of the situation. Where a course of multiple doses is required or otherwise desired, it may be beneficial to administer the peptides, as herein disclosed, via more than one route. For example, it may be desirable to administer a first dose parenterally (e.g., via intramuscular, intravenous; subcutaneous, epidural, intra-articular, intraperitoneal, intracisternal or intrathecal routes of administration) to induce a rapid or acute therapeutic effect in a subject, followed by a subsequent (e.g., second, third, fourth, fifth, etc) dose administered enterally (e.g., orally or rectally) and/or topically (e.g., via transdermal or transmucosal routes of administration) to provide continuing availability of the active agent over an extended period subsequent to the acute phase of treatment. Alternatively, it may be desirable to administer a dose enterally (e.g., orally or rectally), followed by a subsequent (e.g., second, third, fourth, fifth, etc) dose administered parenterally (e.g., via intramuscular, intravenous; subcutaneous, epidural, intra-articular, intraperitoneal, intracisternal or intrathecal routes of administration) and/or topically (e.g., via transdermal or transmucosal routes of administration). Alternatively, it may be desirable to administer a dose topically (e.g., via transdermal or transmucosal routes of administration), followed by a subsequent (e.g., second, third, fourth, fifth, etc) dose administered parenterally (e.g., via intramuscular, intravenous; subcutaneous, epidural, intra-articular, intraperitoneal, intracisternal or intrathecal routes of administration) and/or enterally (e.g., orally or rectally).

The route of administration may suitably be selected on the basis of the type of infection and symptoms thereof, as discussed elsewhere herein. Alternatively, or in addition, the route of administration may suitably be selected having regard to factors such as the subject's general health, age, weight and tolerance (or a lack thereof) for given routes of administration (e.g., where there is a phobia of needles, an alternative route of administration may be selected, such as enteral and/or topical).

It is also to be understood that, where multiple routes of administration are desired, any combination of two or more routes of administration may be used in accordance with the methods disclosed herein. Illustrative examples of suitable combinations include, but are not limited to, (in order of administration), (a) parenteral-enteral; (b) parenteral-topical; (c) parenteral-enteral-topical; (d) parenteral-topical-enteral; (e) enteral-parenteral; (f) enteral-topical; (g) enteral-topical-parenteral; (h) enteral-parenteral-topical; (i) topical-parenteral; (j) topical-enteral; (k) topical-parenteral-enteral; (l) topical-enteral-parenteral; (m) parenteral-enteral-topical-parenteral; (n) parenteral-enteral-topical-enteral; etc.

In an embodiment, the methods comprise (i) parenterally administering to the subject the peptides or compositions, as disclosed herein, and (ii) non-parenterally (i.e, enterally or topically) administering to the subject the peptides or compositions, as disclosed herein, wherein the non-parenteral (enteral or topical) administration is subsequent to the parenteral administration. In an embodiment, the parental administration is selected from the group consisting of intramuscular, a subcutaneous and intravenous. In a further embodiment, the parental administration is subcutaneous. In an embodiment, the non-parental administration is oral.

In an embodiment, the methods disclosed herein comprise (i) parenterally administering to a human subject the peptide of formula (I), or a pharmaceutically acceptable salt thereof, and (ii) orally administering to the human subject the peptide of formula (I), or a pharmaceutically acceptable salt thereof, wherein the oral administration is subsequent to the parenteral administration. In another embodiment, the methods disclosed herein comprise (i) parenterally administering to a human subject the peptide of SEQ ID NO:2, or a pharmaceutically acceptable salt thereof, and (ii) orally administering to the human subject the peptide of SEQ ID NO:2, or a pharmaceutically acceptable salt thereof, wherein the oral administration is subsequent to the parenteral administration. In an embodiment, the parental administration is subcutaneous. In another embodiment, the parental administration is intrathecal.

In an embodiment, the methods disclosed herein comprise (i) parenterally administering to a non-human subject the peptide of formula (II), or a pharmaceutically acceptable salt thereof, and (ii) orally administering to the non-human subject the peptide of formula (II), or a pharmaceutically acceptable salt thereof, wherein the oral administration is subsequent to the parenteral administration. In a further embodiment, the methods disclosed herein comprise (i) parenterally administering to a non-human subject the peptide of SEQ ID NO:7, or a pharmaceutically acceptable salt thereof, and (ii) orally administering to the non-human subject the peptide of SEQ ID NO:7, or a pharmaceutically acceptable salt thereof, wherein the oral administration is subsequent to the parenteral administration. In an embodiment, the non-human subject is selected from the group consisting of a feline, a canine and an equine. In an embodiment, the parental administration is subcutaneous. In another embodiment, the parental administration is intrathecal.

In an embodiment, the methods disclosed herein comprise (i) parenterally administering to a non-human subject the peptide of formula (III), or a pharmaceutically acceptable salt thereof, and (ii) orally administering to the non-human subject the peptide of formula (III), or a pharmaceutically acceptable salt thereof, wherein the oral administration is subsequent to the parenteral administration. In a further embodiment, the methods disclosed herein comprise (i) parenterally administering to a non-human subject the peptide of SEQ ID NO:36, or a pharmaceutically acceptable salt thereof, and (ii) orally administering to the non-human subject the peptide of SEQ ID NO:36, or a pharmaceutically acceptable salt thereof, wherein the oral administration is subsequent to the parenteral administration. In an embodiment, the non-human subject is selected from the group consisting of a feline, a canine and an equine. In an embodiment, the parental administration is subcutaneous. In another embodiment, the parental administration is intrathecal.

In an embodiment, the methods disclosed herein comprise (i) parenterally administering to a non-human subject the peptide of formula (IV), or a pharmaceutically acceptable salt thereof, and (ii) orally administering to the non-human subject the peptide of formula (IV), or a pharmaceutically acceptable salt thereof, wherein the oral administration is subsequent to the parenteral administration. In a further embodiment, the methods disclosed herein comprise (i) parenterally administering to a non-human subject the peptide of SEQ ID NO:41, or a pharmaceutically acceptable salt thereof, and (ii) orally administering to the non-human subject the peptide of SEQ ID NO:41, or a pharmaceutically acceptable salt thereof, wherein the oral administration is subsequent to the parenteral administration. In an embodiment, the non-human subject is selected from the group consisting of a feline, a canine and an equine. In an embodiment, the parental administration is subcutaneous. In another embodiment, the parental administration is intrathecal.

In a further embodiment, the methods disclosed herein comprise (i) parenterally administering to a human subject the peptide of formula (I), or a pharmaceutically acceptable salt thereof, and (ii) topically administering to the human subject the peptide of formula (I), or a pharmaceutically acceptable salt thereof, wherein the topical administration is subsequent to the parenteral administration. In a further embodiment, the methods disclosed herein comprise (i) parenterally administering to a human subject the peptide of SEQ ID NO:2, or a pharmaceutically acceptable salt thereof, and (ii) topically administering to the human subject the peptide of SEQ ID NO:2, or a pharmaceutically acceptable salt thereof, wherein the topical administration is subsequent to the parenteral administration.

In a further embodiment, the methods disclosed herein comprise (i) parenterally administering to a non-human subject the peptide of formula (II), or a pharmaceutically acceptable salt thereof, and (ii) topically administering to the non-human subject the peptide of formula (II), or a pharmaceutically acceptable salt thereof, wherein the topical administration is subsequent to the parenteral administration. In a further embodiment, the methods disclosed herein comprise (i) parenterally administering to a non-human subject the peptide of SEQ ID NO:7, or a pharmaceutically acceptable salt thereof, and (ii) topically administering to the non-human subject the peptide of SEQ ID NO:7, or a pharmaceutically acceptable salt thereof, wherein the topical administration is subsequent to the parenteral administration.

In a further embodiment, the methods disclosed herein comprise (i) parenterally administering to a non-human subject the peptide of formula (III), or a pharmaceutically acceptable salt thereof, and (ii) topically administering to the non-human subject the peptide of formula (III), or a pharmaceutically acceptable salt thereof, wherein the topical administration is subsequent to the parenteral administration. In a further embodiment, the methods disclosed herein comprise (i) parenterally administering to a non-human subject the peptide of SEQ ID NO:36, or a pharmaceutically acceptable salt thereof, and (ii) topically administering to the non-human subject the peptide of SEQ ID NO:36, or a pharmaceutically acceptable salt thereof, wherein the topical administration is subsequent to the parenteral administration.

In a further embodiment, the methods disclosed herein comprise (i) parenterally administering to a non-human subject the peptide of formula (IV), or a pharmaceutically acceptable salt thereof, and (ii) topically administering to the non-human subject the peptide of formula (IV), or a pharmaceutically acceptable salt thereof, wherein the topical administration is subsequent to the parenteral administration. In a further embodiment, the methods disclosed herein comprise (i) parenterally administering to a non-human subject the peptide of SEQ ID NO:41, or a pharmaceutically acceptable salt thereof, and (ii) topically administering to the non-human subject the peptide of SEQ ID NO:41, or a pharmaceutically acceptable salt thereof, wherein the topical administration is subsequent to the parenteral administration.

In an embodiment, the non-human subject is selected from the group consisting of a feline, a canine and an equine. In an embodiment, the parenteral route of administration is subcutaneous. In another embodiment, the topical route of administration is transdermal. In another embodiment, the parenteral administration is subcutaneous and the topical administration is transdermal.

Alternatively, or in addition, the peptides and compositions as herein described may suitably be administered as a controlled release dosage form. Thus, in an embodiment, the methods comprise (i) parenterally administering to the subject the peptides or compositions, as disclosed herein, and (ii) administering to the subject the peptides or compositions, as disclosed herein, as a controlled release dosage form, wherein the controlled release dosage form is administered subsequent to the parenteral administration. In another embodiment, the methods comprise (i) non-parenterally (enterally or topically) administering to the subject the peptides or compositions, as disclosed herein, and (ii) administering to the subject the peptides or compositions, as disclosed herein, as a controlled release dosage form, wherein the controlled release dosage form is administered to the subject subsequent to the non-parenteral administration. In yet another embodiment, the methods comprise (i) enterally administering to the subject the peptides or compositions, as disclosed herein, and (ii) administering to the subject the peptides or compositions, as disclosed herein, as a controlled release dosage form, wherein the controlled release dosage form is administered to the subject subsequent to the enteral administration. In yet another embodiment, the methods comprise (i) topically administering to the subject the peptides or compositions, as disclosed herein, and (ii) administering to the subject the peptides or compositions, as disclosed herein, as a controlled release dosage form, wherein the controlled release dosage form is administered to the subject subsequent to the topical administration. In a preferred embodiment, the controlled release dosage form is formulated for parenteral administration.

Pharmaceutical Compositions

The peptides of formulae (I), (II), (III) and (IV), or pharmaceutically acceptable salts thereof, may be formulated for administration to a subject as a neat chemical. However, in certain embodiments, it may be preferable to formulate the peptides of formulae (I), (II), (III) and (IV), and pharmaceutically acceptable salts thereof, as a pharmaceutical composition, including veterinary compositions. Thus, in another aspect disclosed herein, there is provided a pharmaceutical composition comprising a peptide of formula (I), or a pharmaceutically acceptable salt thereof, as described herein, for use in the treatment of a respiratory tract infection in a subject:

(I)
(SEQ ID NO: 1)
$R^1$-CRSVEGSCG-$R^2$ wherein $R^1$ is selected from the group consisting of YLRIVQ (SEQ ID NO:45), LRIVQ (SEQ ID NO:46), RIVQ (SEQ ID NO:47), IVQ, VQ, and Q, or $R^1$ is absent; and $R^2$ is F (phenylalanine), or $R^2$ is absent.

In an embodiment, the peptide is selected from the group consisting of (SEQ ID NO: 2)
YLRIVQCRSVEGSCGF, (SEQ ID NO: 3)
LRIVQCRSVEGSCGF, (SEQ ID NO: 4)
CRSVEGSCG
and (SEQ ID NO: 5)
CRSVEGSCGF In an embodiment, the peptide is YLRIVQCRSVEGSCGF (SEQ ID NO:2). In an embodiment, the peptide is CRSVEGSCG (SEQ ID NO:4). In an embodiment, the peptide is CRSVEGSCGF (SEQ ID NO:5).

In another aspect disclosed herein, there is provided use of a peptide of formula (I), or a pharmaceutically acceptable salt thereof, as described herein, in the manufacture of a medicament for the treatment of a respiratory tract infection in a subject:

(I)
(SEQ ID NO: 1)
$R^1$-CRSVEGSCG-$R^2$ wherein $R^1$ is selected from the group consisting of YLRIVQ (SEQ ID NO:45), LRIVQ (SEQ ID NO:46), RIVQ (SEQ ID NO:47), IVQ, VQ, and Q, or $R^1$ is absent; and $R^2$ is F (phenylalanine), or $R^2$ is absent.

In an embodiment, wherein the peptide is selected from the group consisting of YLRIVQCRSVEGSCGF (SEQ ID NO:2), LRIVQCRSVEGSCGF (SEQ ID NO:3), CRSVEGSCG (SEQ ID NO:4) and CRSVEGSCGF (SEQ ID NO:5). In an embodiment, the peptide is YLRIVQCRSVEGSCGF (SEQ ID NO:2). In an embodiment, the peptide is CRSVEGSCG (SEQ ID NO:4). In an embodiment, the peptide is CRSVEGSCGF (SEQ ID NO:5).

In another aspect disclosed herein, there is provided a pharmaceutical composition comprising a peptide of formula (II), or a pharmaceutically acceptable salt thereof, for use in the treatment of a respiratory tract infection in a subject:

```
(II)
                    (SEQ ID NO: 6)
R1-CRRFVESSC-R2
```

wherein $R^1$ is selected from the group consisting of YLRVMK (SEQ ID NO:48), LRVMK (SEQ ID NO:49), RVMK (SEQ ID NO:50), VMK, MK, and K, or $R^1$ is absent; and $R^2$ is selected from the group consisting of A (alanine) and AF (alanine-phenylalanine), or $R^2$ is absent.

In an embodiment, the peptide is selected from the group consisting of

```
                    (SEQ ID NO: 7)
YLRVMKCRRFVESSCAF,

                    (SEQ ID NO: 8)
LRVMKCRRFVESSCAF,

                    (SEQ ID NO: 9)
CRRFVESSCAF
and

                    (SEQ ID NO: 10)
CRRFVESSCA
```

In an embodiment, the peptide is YLRVMKCRRFVESSCAF (SEQ ID NO:7). In an embodiment, the peptide is CRRFVESSCAF (SEQ ID NO:9). In an embodiment, the peptide is CRRFVESSCA (SEQ ID NO:10).

In another aspect disclosed herein, there is provided a use of a peptide of formula (II), or a pharmaceutically acceptable salt thereof, in the manufacture of a medicament for the treatment of a respiratory tract infection in a subject:

```
(II)
                    (SEQ ID NO: 6)
R1-CRRFVESSC-R2
```

wherein $R^1$ is selected from the group consisting of YLRVMK (SEQ ID NO:48), LRVMK (SEQ ID NO:49), RVMK (SEQ ID NO:450), VMK, MK, and K, or $R^1$ is absent; and $R^2$ is selected from the group consisting of A (alanine) and AF (alanine-phenylalanine), or $R^2$ is absent.

In an embodiment, the peptide is selected from the group consisting of YLRVMKCRRFVESSCAF (SEQ ID NO:7), LRVMKCRRFVESSCAF (SEQ ID NO:8), CRRFVESSCAF (SEQ ID NO:9) and CRRFVESSCA (SEQ ID NO:10). In an embodiment, the peptide is YLRVMKCRRFVESSCAF (SEQ ID NO:7). In an embodiment, the peptide is CRRFVESSCAF (SEQ ID NO:9). In an embodiment, the peptide is CRRFVESSCA (SEQ ID NO:10).

In another aspect disclosed herein, there is provided a pharmaceutical composition comprising a peptide of formula (III), or a pharmaceutically acceptable salt thereof, for use in the treatment of a respiratory tract infection in a subject:

(III)
(SEQ ID NO: 11)
$R^1$-C-R-$X^1$-$X^2$-P-$X^3$-$X^4$-$X^5$-$X^6$-C-$R^2$ wherein $X^1$, $X^3$, $X^5$, and $X^6$ is an amino acid residue selected from the group consisting of serine, alanine, valine, leucine, isoleucine and glycine;

$X^2$ is arginine or lysine;

$X^4$ is glutamic acid or aspartic acid;

$R^1$ is selected from the group consisting of:

```
S,
                    (SEQ ID NO: 12)
HS,
                    (SEQ ID NO: 13)
GHS,
                    (SEQ ID NO: 14)
PGHS,
                    (SEQ ID NO: 15)
APGHS,
                    (SEQ ID NO: 16)
EAPGHS,
                    (SEQ ID NO: 17)
SEAPGHS,
                    (SEQ ID NO: 18)
SSEAPGHS,
                    (SEQ ID NO: 19)
PSSEAPGHS,
                    (SEQ ID NO: 20)
DPSSEAPGHS,
and
                    (SEQ ID NO: 21)
IDPSSEAPGHS,
```

or $R^1$ is absent; and $R^2$ is selected from the group consisting of

```
S,
                    (SEQ ID NO: 22)
SS,
                    (SEQ ID NO: 23)
SSK,
                    (SEQ ID NO: 24)
SSKF,
                    (SEQ ID NO: 25)
SSKFS,
                    (SEQ ID NO: 26)
SSKFSW,
                    (SEQ ID NO: 27)
SSKFSWD,
                    (SEQ ID NO: 28)
SSKFSWDE,
                    (SEQ ID NO: 29)
SSKFSWDEY,
                    (SEQ ID NO: 30)
SSKFSWDEYE,
```

-continued (SEQ ID NO: 31)
SSKFSWDEYEQ, (SEQ ID NO: 32)
SSKFSWDEYEQY, (SEQ ID NO: 33)
SSKFSWDEYEQYK, (SEQ ID NO: 34)
SSKFSWDEYEQYKK,
and (SEQ ID NO: 35)
SSKFSWDEYEQYKKE, or $R^2$ is absent.

In another aspect disclosed herein, there is provided use of a peptide of formula (III), or a pharmaceutically acceptable salt thereof, in the manufacture of a medicament for the treatment of a respiratory tract infection in a subject:

(III)
(SEQ ID NO: 11)
$R^1$-C-R-$X^1$-$X^2$-P-$X^3$-$X^4$-$X^5$-$X^6$-C-$R^2$ wherein $X^1$, $X^3$, $X^5$, and $X^6$ is an amino acid residue selected from the group consisting of serine, alanine, valine, leucine, isoleucine and glycine;

$X^2$ is arginine or lysine;

$X^4$ is glutamic acid or aspartic acid;

$R^1$ is selected from the group consisting of:

S, (SEQ ID NO: 12)
HS, (SEQ ID NO: 13)
GHS, (SEQ ID NO: 14)
PGHS, (SEQ ID NO: 15)
APGHS, (SEQ ID NO: 16)
EAPGHS, (SEQ ID NO: 17)
SEAPGHS, (SEQ ID NO: 18)
SSEAPGHS, (SEQ ID NO: 19)
PSSEAPGHS, (SEQ ID NO: 20)
DPSSEAPGHS
and (SEQ ID NO: 21)
IDPSSEAPGHS, or $R^1$ is absent; and $R^3$ is selected from the group consisting of

S, (SEQ ID NO: 22)
SS, (SEQ ID NO: 23)
SSK, (SEQ ID NO: 24)
SSKF, (SEQ ID NO: 25)
SSKFS, (SEQ ID NO: 26)
SSKFSW, (SEQ ID NO: 27)
SSKFSWD, (SEQ ID NO: 28)
SSKFSWDE, (SEQ ID NO: 29)
SSKFSWDEY, (SEQ ID NO: 30)
SSKFSWDEYE, (SEQ ID NO: 31)
SSKFSWDEYEQ, (SEQ ID NO: 32)
SSKFSWDEYEQY, (SEQ ID NO: 33)
SSKFSWDEYEQYK, (SEQ ID NO: 34)
SSKFSWDEYEQYKK,
and (SEQ ID NO: 35)
SSKFSWDEYEQYKKE, or $R^2$ is absent.

In an embodiment disclosed herein, the peptide of formula (III) has an amino acid sequence selected from the group consisting of:

(SEQ ID NO: 36)
SCRSRPVESSC;

(SEQ ID NO: 37)
CRSRPVESSC;

(SEQ ID NO: 38)
CRSRPVESSCS;
and (SEQ ID NO: 39)
SCRSRPVESSCS.

In another aspect disclosed herein, there is provided a pharmaceutical composition comprising a peptide of formula (IV) or a pharmaceutically acceptable salt thereof, for use in the treatment of a respiratory tract infection in a subject:

(IV)
(SEQ ID NO: 40)
$R^1$-C-R-I-$X_1$-$X_2$-$X_3$-$X_4$-N-C-$R^2$ wherein $X_1$ is an amino acid residue selected from isoleucine (I) and valine (V);

$X_2$ is an amino acid residue selected from histidine (H) and tyrosine (Y);

$X_3$ is an amino acid residue selected from aspartic acid (D) and asparagine (N);

$X_4$ is an amino acid residue selected from asparagine (N) and serine (S);

$R^1$ is selected from the group consisting of YLKLLK (SEQ ID NO:51), LKLLK (SEQ ID NO:52), KLLK (SEQ ID NO:53), LLK, LL, K or $R^1$ is absent; and $R^2$ is G (glycine), or $R^2$ is absent, or $R^2$ is a pharmaceutically acceptable carrier.

In another aspect disclosed herein, there is provided a use of a peptide of formula (IV) or a pharmaceutically acceptable salt thereof, in the manufacture of a medicament for the treatment of a respiratory tract infection in a subject:

(IV)

(SEQ ID NO: 40)

$R^1$-C-R-I-$X_1$-$X_2$-$X_3$-$X_4$-N-C-$R^2$ wherein $X_1$ is an amino acid residue selected from isoleucine (I) and valine (V);

$X_2$ is an amino acid residue selected from histidine (H) and tyrosine (Y);

$X_3$ is an amino acid residue selected from aspartic acid (D) and asparagine (N);

$X_4$ is an amino acid residue selected from asparagine (N) and serine (S);

$R^1$ is selected from the group consisting of YLKLLK (SEQ ID NO:51), LKLLK (SEQ ID NO:52), KLLK (SEQ ID NO:53), LLK, LL, K or $R^1$ is absent; and $R^2$ is G (glycine), or $R^2$ is absent, or $R^2$ is a pharmaceutically acceptable carrier.

In an embodiment, the peptide of formula (IV) is selected from the group consisting of amino acid sequence CRIIHNNNC (SEQ ID NO:41), CRIIHNNNCG (SEQ ID NO:42), CRIVYDSNC (SEQ ID NO:43) and CRIVYDSNCG (SEQ ID NO:44).

As noted elsewhere herein, the peptides of formulae (I), (II), (III) and (IV), or pharmaceutically acceptable salts thereof, may be administered together, either sequentially or in combination (e.g., as an admixture), with one or more other active agents appropriate to the underlying condition to be treated. For example, the compositions disclosed herein may be formulated for administration together, either sequentially or in combination (e.g., as an admixture), with one or more vaccine compositions aimed at raising an immune response against the pathogen or the suspected pathogen towards which the treatment is targeted. Combination treatments of this nature can be advantageous, for example, by alleviating the respiratory tract infection or a symptom thereof while also raising an immune response to the pathogen in the subject to combat further infection.

In an embodiment, the composition further comprises a pharmaceutically acceptable carrier, excipient or diluent, as described elsewhere herein. In an embodiment, the composition is formulated for oral administration.

Illustrative examples of suitable pharmaceutical formulations include those suitable for enteral or parenteral administration, illustrative examples of which are described elsewhere herein, including oral, rectal, buccal, sublingual, vaginal, nasal, topical (e.g., transdermal), intramuscular, subcutaneous, intravenous, epidural, intra-articular and intrathecal.

The peptides of formulae (I), (II), (III) and (IV), or pharmaceutically acceptable salts thereof, may suitably be prepared as pharmaceutical compositions and unit dosage forms to be employed as solids (e.g., tablets or filled capsules) or liquids (e.g., solutions, suspensions, emulsions, elixirs, or capsules filled with the same) for oral use, in the form of ointments, suppositories or enemas for rectal administration, in the form of sterile injectable solutions for parenteral use (e.g., intramuscular, subcutaneous, intravenous, epidural, intra-articular and intrathecal administration); or in the form of ointments, lotions, creams, gels, patches, sublingual strips or films, and the like for parenteral (e.g., topical, buccal, sublingual, vaginal) administration. In an embodiment, the peptides of formulae (I), (II), (III) and (IV), or pharmaceutically acceptable salts thereof, are formulated for topical (e.g., transdermal) delivery. Suitable transdermal delivery systems will be familiar to persons skilled in the art, illustrative examples of which are described by Prausnitz and Langer (2008; *Nature Biotechnol.* 26(11):1261-1268), the contents of which are incorporated herein by reference. In another embodiment, the peptides of formulae (I), (II), (III) and (IV), or pharmaceutically acceptable salts thereof, are formulated for sublingual or buccal delivery. Suitable sublingual and buccal delivery systems will be familiar to persons skilled in the art, illustrative examples of which include dissolvable strips or films, as described by Bala et al. (2013; *Int. J. Pharm. Investig.* 3(2):67-76), the contents of which are incorporated herein by reference.

Suitable pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. The peptides of formulae (I), (II), (III) and (IV), or pharmaceutically acceptable salts thereof, as described herein, can be formulated for administration in a wide variety of enteral, topical and/or parenteral dosage forms. Suitable dosage forms may comprise, as the active component, either a peptide of formula (I), a peptide of formula (II), a peptide of formula (III), a peptide of formula (IV), pharmaceutically acceptable salts thereof, or combinations of any of the foregoing, as herein described.

In an embodiment, the composition is formulated for oral administration to a human. In another embodiment, the composition is formulated for oral administration to a non-human subject. In yet another embodiment, the composition is formulated for oral administration to a non-human subject selected from the group consisting of a feline, a canine and an equine.

In another embodiment, the composition is formulated for parenteral administration to a human. In another embodiment, the composition is formulated for parenteral administration to a non-human subject. In yet another embodiment, the composition is formulated for parenteral administration to a non-human subject selected from the group consisting of a feline, a canine and an equine. In an embodiment, the parenteral administration is subcutaneous administration.

In another embodiment, the composition is formulated for topical administration to a human. In another embodiment, the composition is formulated for topical administration to a non-human subject. In yet another embodiment, the composition is formulated for topical administration to a non-human subject selected from the group consisting of a feline, a canine and an equine. In an embodiment, the topical administration is transdermal.

In another embodiment, the composition is formulated as a controlled release dosage form to be administered to a human. In another embodiment, the composition is formulated as a controlled release dosage form to be administered to a non-human subject. In yet another embodiment, the composition is formulated as a controlled release dosage form to be administered to a non-human subject selected from the group consisting of a feline, a canine and an equine. Illustrative examples of suitable controlled release dosage forms are described elsewhere herein.

For preparing pharmaceutical compositions of the peptides of formulae (I), (II), (III) and (IV), or pharmaceutically acceptable salts thereof, pharmaceutically acceptable carriers can be either solid or liquid. Illustrative examples of solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material. In powders, the carrier may be a finely divided solid which is in a mixture with the finely divided active component. In tablets, the active component may be mixed with the carrier having the necessary binding capacity in suitable proportions and compacted in the shape and size desired.

In some embodiments, the powders and tablets contain from five or ten to about seventy percent of the active compound. Illustrative examples of suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term “preparation” is intended to include the formulation of the active compound with encapsulating material, providing a capsule in which the active component, with or without carriers, is surrounded by a carrier. Similarly, cachets and lozenges are also envisaged herein. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The peptides of formulae (I), (II), (III) and (IV), or pharmaceutically acceptable salts thereof, as described herein, may be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active compound(s) may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also contemplated herein are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis, the peptides of formulae (I), (II) or (III), or pharmaceutically acceptable salts thereof, as described herein, may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the peptides used in the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively, or in addition, the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently, the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the peptide will generally have a small particle size for example of the order of 1 to 10 microns or less. Such a particle size may be obtained by means known in the art, for example by micronization.

When desired, formulations adapted to give controlled or sustained release of the active ingredient may be employed, as described elsewhere herein.

In an embodiment, the pharmaceutical preparations, as herein described, are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In an embodiment, the compositions disclosed herein are formulated for oral administration to a human. In yet another embodiment, the compositions disclosed herein are formulated for oral administration to a non-human. In a further embodiment, the compositions disclosed herein are formulated for oral administration to a non-human selected from the group consisting of a feline, a canine and an equine.

In another embodiment, the peptide of formula (I), or a pharmaceutically acceptable salt thereof, as disclosed herein, is formulated for oral administration to a human subject. In another embodiment, the peptide of formula (I), or a pharmaceutically acceptable salt thereof, as disclosed herein, is formulated for oral administration to a non-human subject. In yet another embodiment, the peptide of formula (I), or a pharmaceutically acceptable salt thereof, as disclosed herein, is formulated for oral administration to a non-human subject selected from the group consisting of a feline, a canine and an equine.

In another embodiment, the peptide of formula (I), or a pharmaceutically acceptable salt thereof, as disclosed herein, is formulated for topical administration to a human subject. In yet another embodiment, the peptide of formula (I), or a pharmaceutically acceptable salt thereof, as disclosed herein, is formulated for topical administration to a non-human subject. In another embodiment, the peptide of formula (I), or a pharmaceutically acceptable salt thereof, as disclosed herein, is formulated for topical administration to a non-human subject selected from the group consisting of a feline, a canine and an equine. In an embodiment, the topical administration is transdermal.

In another embodiment, the peptide of formula (I), or a pharmaceutically acceptable salt thereof, as disclosed herein, is formulated for administration to a human subject as a controlled release dosage form. In yet another embodiment, the peptide of formula (I), or a pharmaceutically acceptable salt thereof, as disclosed herein, is formulated for administration to a non-human subject as a controlled release dosage form. In another embodiment, the peptide of formula (I), or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide of formula (II), or a pharmaceutically acceptable salt thereof, as disclosed herein, are formulated for oral administration to a non-human subject. In yet another embodiment, the peptide of formula (II), or a pharmaceutically acceptable salt thereof, as disclosed herein, is formulated for oral administration to a non-human subject selected from the group consisting of a feline, a canine and an equine.

In another embodiment, the peptide of formula (II), or a pharmaceutically acceptable salt thereof, as disclosed herein, is formulated for topical administration to a non-human subject. In yet another embodiment, the peptide of formula (II), or a pharmaceutically acceptable salt thereof, as disclosed herein, is formulated for topical administration to a non-human subject selected from the group consisting of a feline, a canine and an equine. In an embodiment, the topical administration is transdermal.

In another embodiment, the peptide of formula (II), or a pharmaceutically acceptable salt thereof, as disclosed herein, is formulated for administration to a human subject as a controlled release dosage form. In yet another embodiment, the peptide of formula (II), or a pharmaceutically acceptable salt thereof, as disclosed herein, is formulated for administration to a non-human subject as a controlled release dosage form. In another embodiment, the peptide of formula (II), or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide of formula (III), or a pharmaceutically acceptable salt thereof, as disclosed herein, are formulated for oral administration to a non-human subject. In yet another embodiment, the peptide of formula (III), or a pharmaceutically acceptable salt thereof, as disclosed herein, is formulated for oral administration to a non-human subject selected from the group consisting of a feline, a canine and an equine.

In another embodiment, the peptide of formula (III), or a pharmaceutically acceptable salt thereof, as disclosed herein, is formulated for topical administration to a non-human subject. In yet another embodiment, the peptide of formula (III), or a pharmaceutically acceptable salt thereof, as disclosed herein, is formulated for topical administration to a non-human subject selected from the group consisting of a feline, a canine and an equine. In an embodiment, the topical administration is transdermal.

In another embodiment, the peptide of formula (III), or a pharmaceutically acceptable salt thereof, as disclosed herein, is formulated for administration to a human subject as a controlled release dosage form. In yet another embodiment, the peptide of formula (III), or a pharmaceutically acceptable salt thereof, as disclosed herein, is formulated for administration to a non-human subject as a controlled release dosage form. In another embodiment, the peptide of formula (III), or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide of formula (IV), or a pharmaceutically acceptable salt thereof, as disclosed herein, are formulated for oral administration to a non-human subject. In yet another embodiment, the peptide of formula (IV), or a pharmaceutically acceptable salt thereof, as disclosed herein, is formulated for oral administration to a non-human subject selected from the group consisting of a feline, a canine and an equine.

In another embodiment, the peptide of formula (IV), or a pharmaceutically acceptable salt thereof, as disclosed herein, is formulated for topical administration to a non-human subject. In yet another embodiment, the peptide of formula (IV), or a pharmaceutically acceptable salt thereof, as disclosed herein, is formulated for topical administration to a non-human subject selected from the group consisting of a feline, a canine and an equine. In an embodiment, the topical administration is transdermal.

In another embodiment, the peptide of formula (IV), or a pharmaceutically acceptable salt thereof, as disclosed herein, is formulated for administration to a human subject as a controlled release dosage form. In yet another embodiment, the peptide of formula (III), or a pharmaceutically acceptable salt thereof, as disclosed herein, is formulated for administration to a non-human subject as a controlled release dosage form. In another embodiment, the peptide of formula (IV), or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide of SEQ ID NO:2, or a pharmaceutically acceptable salt thereof, is formulated for oral administration to a human. In another embodiment, the peptide of SEQ ID NO:2, or a pharmaceutically acceptable salt thereof, is formulated for oral administration to a non-human. subject. In yet another embodiment, the peptide of SEQ ID NO:2, or a pharmaceutically acceptable salt thereof, is formulated for oral administration to a non-human subject selected from the group consisting of a feline, a canine and an equine.

In another embodiment, the peptide of SEQ ID NO:2, or a pharmaceutically acceptable salt thereof, as disclosed herein, is formulated for topical administration to a human subject. In yet another embodiment, the peptide of SEQ ID NO:2, or a pharmaceutically acceptable salt thereof, as disclosed herein, is formulated for topical administration to a non-human subject. In another embodiment, the peptide of SEQ ID NO:2, or a pharmaceutically acceptable salt thereof, as disclosed herein, is formulated for topical administration to a non-human subject selected from the group consisting of a feline, a canine and an equine. In an embodiment, the topical administration is transdermal.

In another embodiment, the peptide of SEQ ID NO:2, or a pharmaceutically acceptable salt thereof, as disclosed herein, is formulated for administration to a human subject as a controlled release dosage form. In yet another embodiment, the peptide of SEQ ID NO:2, or a pharmaceutically acceptable salt thereof, as disclosed herein, is formulated for administration to a non-human subject as a controlled release dosage form. In another embodiment, the peptide of SEQ ID NO:2, or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide of SEQ ID NO:7, or a pharmaceutically acceptable salt thereof, is formulated for oral administration to a non-human. subject. In yet another embodiment, the peptide of SEQ ID NO:7, or a pharmaceutically acceptable salt thereof, is formulated for oral administration to a non-human subject selected from the group consisting of a feline, a canine and an equine.

In another embodiment, the peptide of SEQ ID NO:7, or a pharmaceutically acceptable salt thereof, is formulated for topical administration to a non-human. subject. In yet another embodiment, the peptide of SEQ ID NO:7, or a pharmaceutically acceptable salt thereof, is formulated for topical administration to a non-human subject selected from the group consisting of a feline, a canine and an equine. In an embodiment, the topical administration is transdermal.

In another embodiment, the peptide of SEQ ID NO:7, or a pharmaceutically acceptable salt thereof, as disclosed herein, is formulated for administration to a human subject as a controlled release dosage form. In yet another embodiment, the peptide of SEQ ID NO:7, or a pharmaceutically acceptable salt thereof, as disclosed herein, is formulated for administration to a non-human subject as a controlled release dosage form. In another embodiment, the peptide of SEQ ID NO:7, or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide of SEQ ID NO:36, or a pharmaceutically acceptable salt thereof, is formulated for oral administration to a non-human. subject. In yet another embodiment, the peptide of SEQ ID NO:36, or a pharmaceutically acceptable salt thereof, is formulated for oral administration to a non-human subject selected from the group consisting of a feline, a canine and an equine.

In another embodiment, the peptide of SEQ ID NO:36, or a pharmaceutically acceptable salt thereof, is formulated for topical administration to a non-human. subject. In yet another embodiment, the peptide of SEQ ID NO:36, or a pharmaceutically acceptable salt thereof, is formulated for topical administration to a non-human subject selected from the group consisting of a feline, a canine and an equine. In an embodiment, the topical administration is transdermal.

In another embodiment, the peptide of SEQ ID NO:36, or a pharmaceutically acceptable salt thereof, as disclosed herein, is formulated for administration to a human subject as a controlled release dosage form. In yet another embodiment, the peptide of SEQ ID NO:36, or a pharmaceutically acceptable salt thereof, as disclosed herein, is formulated for administration to a non-human subject as a controlled release dosage form. In another embodiment, the peptide of SEQ ID NO:36, or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

In another embodiment, the peptide of SEQ ID NO:41, or a pharmaceutically acceptable salt thereof, is formulated for oral administration to a human. In another embodiment, the peptide of SEQ ID NO:41, or a pharmaceutically acceptable salt thereof, is formulated for oral administration to a non-human. subject. In yet another embodiment, the peptide of SEQ ID NO:41, or a pharmaceutically acceptable salt thereof, is formulated for oral administration to a non-human subject selected from the group consisting of a feline, a canine and an equine.

In another embodiment, the peptide of SEQ ID NO:41, or a pharmaceutically acceptable salt thereof, as disclosed herein, is formulated for topical administration to a human subject. In yet another embodiment, the peptide of SEQ ID NO:41, or a pharmaceutically acceptable salt thereof, as disclosed herein, is formulated for topical administration to a non-human subject. In another embodiment, the peptide of SEQ ID NO:41, or a pharmaceutically acceptable salt thereof, as disclosed herein, is formulated for topical administration to a non-human subject selected from the group consisting of a feline, a canine and an equine. In an embodiment, the topical administration is transdermal.

In another embodiment, the peptide of SEQ ID NO:41, or a pharmaceutically acceptable salt thereof, as disclosed herein, is formulated for administration to a human subject as a controlled release dosage form. In yet another embodiment, the peptide of SEQ ID NO:41, or a pharmaceutically acceptable salt thereof, as disclosed herein, is formulated for administration to a non-human subject as a controlled release dosage form. In another embodiment, the peptide of SEQ ID NO:41, or a pharmaceutically acceptable salt thereof, as disclosed herein, is formulated for administration to a non-human subject as a controlled release dosage form, wherein the non-human subject is selected from the group consisting of a feline, a canine and an equine. In an embodiment, the controlled release dosage form is formulated for parenteral administration.

As noted elsewhere herein, several (i.e., multiple) divided doses may be administered daily, weekly, monthly or other suitable time intervals, or the dose may be proportionally reduced as indicated by the exigencies of the situation. Where a course of multiple doses is required or otherwise desired, the compositions disclosed herein can be suitably formulated for administration via said multiple routes. For example, it may be desirable to administer a first dose parenterally (e.g., intramuscular, intravenously; subcutaneously, etc) to induce a rapid or otherwise acute therapeutic effect in a subject, followed by a subsequent (e.g., second, third, fourth, fifth, etc) dose administered non-parenterally (e.g., enterally and/or topically) to provide continuing availability of the active agent over an extended period subsequent to the acute phase of treatment. Thus, in an embodiment, the peptides and compositions, as disclosed herein, are formulated for parenteral administration to the subject as a first dose (i.e., as a parenteral dosage form) and formulated for non-parenteral administration to the subject after the first dose (e.g., as an enteral and/or topical dosage form). In an embodiment, the parental administration is selected from the group consisting of intramuscular, subcutaneous and intravenous. In a further embodiment, the parental administration is subcutaneous.

In another embodiment, the enteral administration is oral administration. Thus, in an embodiment, the peptides and compositions, as disclosed herein, are formulated for parenteral administration to the subject as a first dose and formulated for oral administration to the subject after the first dose (i.e., as an oral dosage form).

In another embodiment, the enteral administration is topical administration. Thus, in an embodiment, the peptides and compositions, as disclosed herein, are formulated for parenteral administration to the subject as a first dose and formulated for topical administration to the subject after the first dose (i.e., as an oral dosage form). In an embodiment, the topical administration is transdermal administration.

In another embodiment, it may be desirable to administer a first dose parenterally (e.g., intramuscular, intravenously; subcutaneously, etc) to induce a rapid or otherwise acute therapeutic effect in a subject, followed by a subsequent (e.g., second, third, fourth, fifth, etc) administration of a controlled release dosage form, as described elsewhere herein, to provide a controlled release of the active agent over an extended period subsequent to the acute phase of treatment. Thus, in another embodiment, the peptides and compositions, as disclosed herein, are formulated for parenteral administration to the subject as a first dose and formulated as a controlled release dosage form to be administered to the subject after the first dose. In an embodiment, the controlled release dosage form is formulated for parental administration.

It may also be desirable to administer a first dose enterally (e.g., orally or rectally), followed by a subsequent (e.g., second, third, fourth, fifth, etc) dose administered topically (e.g., transdermally). Thus, in an embodiment, the peptides and compositions, as disclosed herein, are formulated for enteral administration to the subject as a first dose (i.e., as an enteral dosage form; oral or rectal) and formulated for topical administration to the subject after the first dose (e.g., as a transdermal or transmucosal dosage form). In another embodiment, the peptides and compositions, as disclosed herein, are formulated for topical administration selected from the group consisting of transdermal and transmucosal administration. In a further embodiment, the peptides and compositions, as disclosed herein, are formulated for transdermal administration.

In yet another embodiment, it may be desirable to administer the peptides or compositions, as disclosed herein, enterally (e.g., orally or rectally) as a first dose, followed by a subsequent (e.g., second, third, fourth, fifth, etc) dose as a controlled release dosage form, as described elsewhere herein. Thus, in an embodiment, the peptides and compositions, as disclosed herein, are formulated for administration as a first dose enterally and formulated for administration as a controlled release dosage form, wherein the controlled release dosage form is formulated for administration subsequent to the first dose. In an embodiment, the enteral dose is formulated for oral administration. In another embodiment, the controlled release dosage form is formulated for parenteral administration.

In an embodiment, it may be desirable to administer the peptides or compositions, as disclosed herein, topically (e.g., orally or rectally) as a first dose, followed by a subsequent (e.g., second, third, fourth, fifth, etc) dose as a controlled release dosage form, as described elsewhere herein. Thus, in an embodiment, the peptides and compositions, as disclosed herein, are formulated for topical administration as a first dose and formulated for administration as a controlled release dosage form, wherein the controlled release dosage form is formulated for administration subsequent to the first topical dose. In an embodiment, the topical dose is formulated for transdermal administration. In another embodiment, the controlled release dosage form is formulated for parenteral administration.

The invention will now be described with reference to the following Examples which illustrate some preferred aspects of the present invention. However, it is to be understood that the particularity of the following description of the invention is not to supersede the generality of the preceding description of the invention.

EXAMPLES

Example 1: Case Study 1

The subject is a 58 year old male who presented with flu-like symptoms. The subject reported to have been free of flu-like symptoms over the past 8 years.

The subject developed a very sore throat. On awakening the next day, the sore throat was more severe and his nose was running (rhinorrhea) and becoming worse throughout the day. Other symptoms that developed during the day included:

- a persistent deep phlegmy cough;
- high temperature;
- body sweats;
- chills;
- muscle soreness; and
- fatigue.

Later that evening, the subject developed a loss of appetite, and an exacerbation of chills, body sweats, rhinorrhoea and persistent coughing. At around 8 pm that evening, the subject was administered ~1 mg AOD9604 (SEQ ID NO:2), orally.

On the day of treatment, the subject recalls falling asleep and waking about 7 hours later, at which point he recalls the only remaining symptoms were a runny nose and a slight cough. All other symptoms had gone. The subject fell back asleep and awoke a few hours later feeling great, except for a slightly runny nose and dry cough, which were reported to have cleared up during the day.

Example 2: Case Study 2

The subject is a 60 year old male who in the afternoon presented with the flu, with symptoms including a persistent deep phlegmy cough, high temperature, body sweats, chills, muscle soreness and fatigue. The subject was administered ~1 mg AOD9604 (SEQ ID NO:2), orally. The subject recalls sleeping well that evening.

By the morning, all symptoms of the flu had disappeared except for a slight runny nose and a dry cough. The subject recalls sleeping well that evening.

The subject awoke the following day and reported to be symptom-free around 24 hours later.

The above case studies demonstrate that AOD9604 (SEQ ID NO:2) is capable of alleviating the symptoms of respiratory tract infection by a virus.

Example 3: Naturally-Derived Cyclic Peptides Limit Virus Replication and Severe Disease in a Mouse Model of Influenza a Infection The prophylactic and therapeutic potential of synthetic human growth hormone (GH) fragment LAT8881 (SEQ ID NO:2) and its metabolite, LAT9991F (which encompasses the cyclic peptide motif; SEQ ID NO:5) to limit severe IAV infection was evaluated. The effectiveness of compound treatment at reducing viral replication, hyperinflammation and disease was investigated in a preclinical model of severe IAV infection.

Materials and Methods

A. Compounds

LAT8881 is a 16-amino acid synthetic form of the C-terminal fragment of human GH (H-YLRIVQCRSVEGSCGF-OH) (SEQ ID NO:2) which contains an additional N-terminal tyrosine residue and two cysteine residues linked by a disulphide bond. LAT9991F is a 10-amino acid synthetic peptide (H-CRSVEGSCGF-OH) (SEQ ID NO:5), which is a truncated form and a known stable metabolite of LAT8881 in human serum. LAT7771 is a 10-amino acid structural homologue (H-CRIIHNNNC-OH) (SEQ ID NO:41), derived from Prolactin. The cysteine residues in both LAT9991F and LAT7771 were also disulphide linked. All peptides were synthesised by Auspep (Melbourne, Australia).

B. Influenza Virus Infection of Mice 6-8 week old C57BL/6 male mice were maintained in the Specific Pathogen Free Physical Containment Level 2 (PC2) Animal Research Facility at the Monash Medical Centre. All experimental procedures were approved by the Hudson Animal Ethics Committee and experimental procedures carried out in accordance with approved guidelines. The IAV strain used in this study was HKx31 (H3N2), which is a high-yielding reassortant of A/PR/8/34 (H1N1) that carries the surface glycoproteins of A/Aichi/2/1968 (H3N2). HKx31 was grown in 10-day embryonated chicken eggs by standard procedures and titrated on Madin-Darby Canine Kidney (MDCK) cells.

For virus infection studies, groups of 8 male C57BL/6 mice were randomized. Mice were lightly anesthetised and infected intranasally with 105 PFU of HKx31 (H3N2) in 50 μl PBS (previously shown to induce severe disease (Rosli et al., 2019; Tate et al., 2016). Mice were treated at the time points indicated with LAT8881, LAT9991F or LAT7771 (5 or 20 mg/kg; as indicated) via the intranasal route. Control mice were treated with PBS alone. Mice were weighed daily and assessed for visual signs of clinical disease, including inactivity, ruffled fur, laboured breathing, and huddling behaviour. Animals that lost ≥20% of their original body weight or displayed severe clinical signs of disease were euthanised. Bronchoalveolar lavage (BAL) fluid was immediately obtained following euthanisation by flushing the lungs three times with 1 mL of PBS. Lungs were then removed and frozen immediately in liquid nitrogen. Titres of infectious virus in lung homogenates were determined by standard plaque assay on MDCK cells.

C. Quantification of Cytokines in Mouse BAL Fluid and Sera

To detect cytokines, BAL fluid was collected and stored at −80° C. Levels of IL-6, MCP-1/CCL2, IFNγ, IL-10, IL-12p70, and TNFα proteins were determined by cytokine bead array (CBA) using the mouse inflammation kit (Becton Dickinson). Levels of mouse IFNα were determined by sandwich ELISA using mouse monoclonal clone F18 (Thermo Scientific) and rabbit polyclonal antibodies (PBL) (Thomas et al., 2014). Levels of mouse IFNβ were determined by sandwich ELISA using mouse monoclonal clone 7F-D3 (Abcam) and rabbit polyclonal antibodies (PBL) (Thomas et al., 2014). Mouse IFN $\lambda_{2/3}$ was quantified by ELISA (R&D Systems).

D. Recovery and Characterization of Leukocytes from Mice

For flow cytometric analysis, BAL cells were treated with red blood cell lysis buffer (Sigma Aldrich) and cell numbers and viability assessed via trypan blue exclusion using a haemocytometer. BAL cells were incubated with Fc block (2.4G2; eBiosciences), followed by staining with fluorochrome-conjugated monoclonal antibodies to Ly6C, Ly6G, CD11c and I-$A^b$ (MHC-II) (BD Biosciences, USA). Neutrophils ($Ly6G^+$), macrophages ($CD11c^+$ I-$A^{b\ low}$), dendritic cells (DC; $CD11c^+$ I-$A^{b\ high}$), inflammatory macrophages ($Ly6G^-$ $Ly6C^+$) were quantified by flow cytometry, as described previously (Rosli et al., 2019; Tate et al., 2016).

Live cells (propidium iodide negative) were analysed using a BD FACS Canto II flow cytometer (BD Biosciences) and FlowJo software (BD Biosciences).

E. Assessment of Lung Oedema and Vascular Leakage

The lung wet to dry weight ratio was used as an index of fluid accumulation in the lung. After euthanasia of mice, the lungs were surgically dissected, blotted dry, and weighed immediately (wet weight). The lung tissue was then dried in an oven at 55° C. for 72 hours and reweighed as dry weight. The ratio of wet to dry weight was calculated for each animal to assess tissue oedema (Tate et al., 2009; Tate et al., 2010). The concentration of protein in cell-free BAL supernatant was measured by adding Bradford protein dye (Tate et al., 2009; Tate et al., 2010). A standard curve using bovine serum albumin was constructed, and the optical density (OD) was determined at 595 nm.

F. Data and Statistical Analysis

The data and statistical analysis in this study comply with the recommendations on experimental design and analysis in pharmacology (Curtis et al., 2018). When comparing three or more sets of values, a one-way analysis of variance (ANOVA) was used with Tukey's post-hoc analysis. A Student's t-test was used when comparing 2 values (two-tailed, two-sample equal variance). Survival proportions were compared using the Mantel-Cox log-rank test. A p value <0.05 was considered statistically significant.

Results

Prophylactic Treatment with LAT8881 Improves Survival During Severe IAV Infection Given the urgent need to development new therapeutics for severe respiratory IAV and SARS-CoV-2 infections, the potential of LAT8881, a synthetic C-terminal fragment of growth hormone (FIG. 1A) to protect mice from severe IAV infection was examined. C57BL/6 mice were treated intranasally with LAT8881 (20 mg/kg) 24 hours prior to infection with $10^5$ PFU of HKx31 H3N2 IAV. Mice received additional LAT8881 every 48 hours following the initial treatment and control IAV-infected mice received PBS alone. LAT8881 treatment of IAV-infected mice reduced clinical signs of disease including weight loss (FIG. 1B), limited mobility, laboured breathing, and significantly improved survival of mice from 0% to approximately 30% of the cohort (FIG. 1C). Importantly, treatment of uninfected mice with LAT8881 did not result in weight loss or any clinical signs of disease (FIG. 1B, C).

Prophylactic Treatment with LAT8881 Limits Viral Replication and Inflammation During Severe IAV Infection Severe and fatal IAV infections are characterised by excessive pulmonary inflammation and cellular infiltrates. Having established that prophylactic treatment of mice with LAT8881 improves survival following IAV infection (FIG. 1), viral loads and airway cellular infiltrates were examined, as well as pro-inflammatory cytokines in BAL fluid and sera on day 4 post-infection (the day on which the majority of control IAV-infected mice approached the ethical humane endpoint of 20% weight loss). Treatment of mice with LAT8881 24 hours prior to IAV infection and every 48 hours thereafter, resulted in a significant 1.6-fold reduction in infectious viral loads in the lung (FIG. 2A). Of note, LAT8881 had no direct antiviral properties against IAV or SARS-CoV-2 infection in vitro (Supplementary FIG. 1B). In particular, LAT8881 treatment of human PBECs had no significant impact on the levels of infectious virus in cell supernatants 24 hours following HKx31 infection (Supplementary FIG. 1A). LAT8881 also did not alter SARS-CoV-2 infection of Vero cells as measured by a cytopathic effect inhibition assay (Supplementary FIG. 1B).

Figure 2:
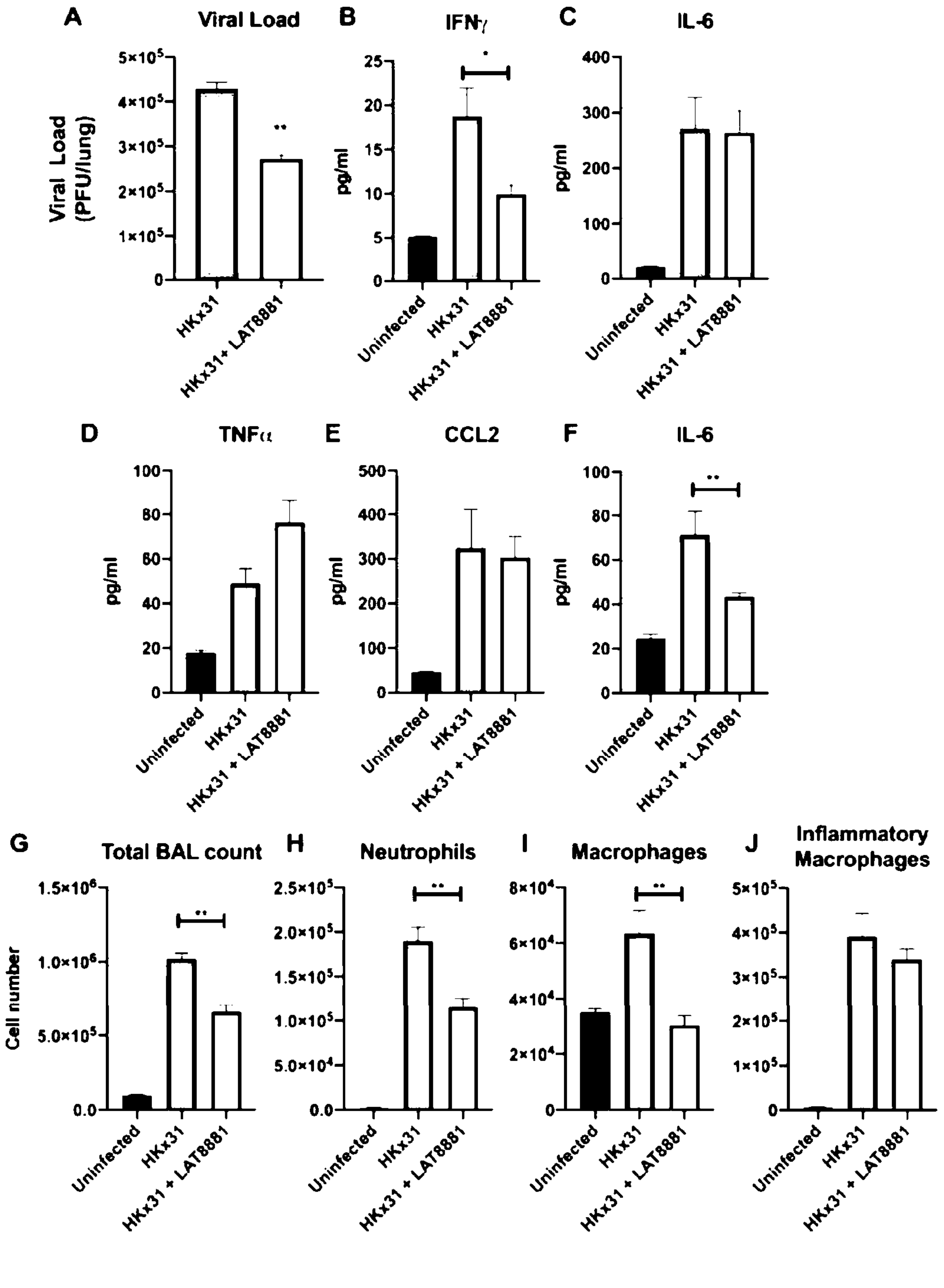
FIG. 2 shows that prophylactic and recurrent LAT8881 treatment limits IAV disease severity. Groups of 8 C57BL/6 mice were treated with LAT8881 (20 mg/kg) via the intranasal route 24 hours prior to intranasal infection with 105 PFU of HKx31 IAV. Mice received additional LAT8881 treatments every 48 hours following the initial treatment. IAV-infected control mice received PBS alone and uninfected controls were also included for comparison. On day 4 post-infection mice were euthanised. (A) Viral loads in the lung were measured by a standard plaque assay. (B-E) Pro-inflammatory cytokine levels in BAL fluid were determined by CBA. (F) Levels of IL-6 in serum were determined by CBA. (G) Total numbers of leukocytes in BAL were determined by viable cell counts and (H-J) Ly6G+ neutrophils, total CD11c+ I-Ab low macrophages and Ly6C+ inflammatory macrophages in BAL were determined by flow cytometry. Data presented as the mean±SEM from 8 mice per group. *p<0.05, **p<0.01, HKx31 vs HKx31+LAT8881, One-way ANOVA.

In addition to reduced viral loads in the lung, LAT8881 significantly reduced levels of IFNγ in BAL fluid (2-fold; FIG. 2B) and IL-6 in the serum (1.5-fold; FIG. 2F). Interestingly, the concentration of IL-6 (FIG. 2C), TNFα (FIG. 2D), CCL2 (FIG. 2E), IL-10 and IL-12p70 (data not shown) in BAL fluid of LAT8881-treated mice was comparable with PBS-treated IAV infected controls. Additionally, no significant differences were observed in levels of type I (IFNα, IFNβ) and III (IFN $\lambda_{2/3}$) IFNs (data not shown). Total BAL cellularity was significantly reduced in LAT8881-treated mice (FIG. 2G), with significantly fewer neutrophils and macrophages present at day 4 post-infection (FIG. 2H-I). By contrast, no significant numerical difference in inflammatory Ly6C$^+$ macrophages (FIG. 2J) or dendritic cells was observed in the airways of infected cohorts. Annexin V and PI straining of BAL cells revealed no significant differences in leukocyte cell death (Supplementary FIG. 2). Collectively, these data suggest that prophylactic LAT8881 treatment can limit viral replication and inflammation in the airways and serum, which would otherwise promote severe IAV disease.

Figure 3:
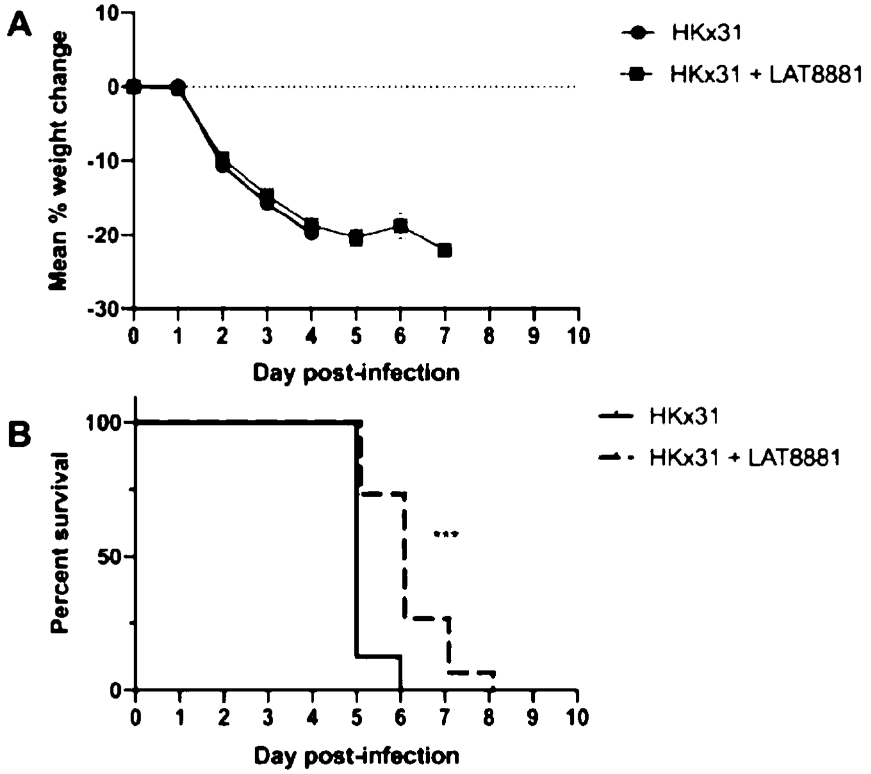
FIG. 3 shows that therapeutic LAT8881 treatment during severe IAV infection improves survival. Groups of 16 C57BL/6 mice were infected intranasally with 105 PFU of HKx31 IAV. Mice were treated with LAT8881 (20 mg/kg) via the intranasal route 24 hours following infection and then every 48 hours. IAV-infected control mice received PBS alone. (A) Mouse weights were recorded daily and results are expressed as mean percent weight change ±SEM. (B) Survival curves are shown. ***p<0.001 HKx31 vs HKx31+LAT8881, Mantel-Cox log-rank test.

Therapeutic Treatment with LAT8881 Improves Survival During Severe IAV Infection Having established prophylactic treatment of mice with LAT8881 protects against severe IAV infection (FIG. 1-2), the ability of therapeutic treatment to limit IAV disease was examined. Mice received intranasal LAT8881 (20 mg/kg) 24 hours following infection with 105 PFU HKx31, with additional treatments at 48 hour intervals. As before, control IAV-infected mice received PBS alone. Therapeutic LAT8881 treatment delayed the onset of clinical signs of severe disease including weight loss (FIG. 3A), limited mobility and laboured breathing. In addition, LAT8881 treatment significantly delayed IAV-associated lethality by 48-72 hours (FIG. 3B).

Figure 4:
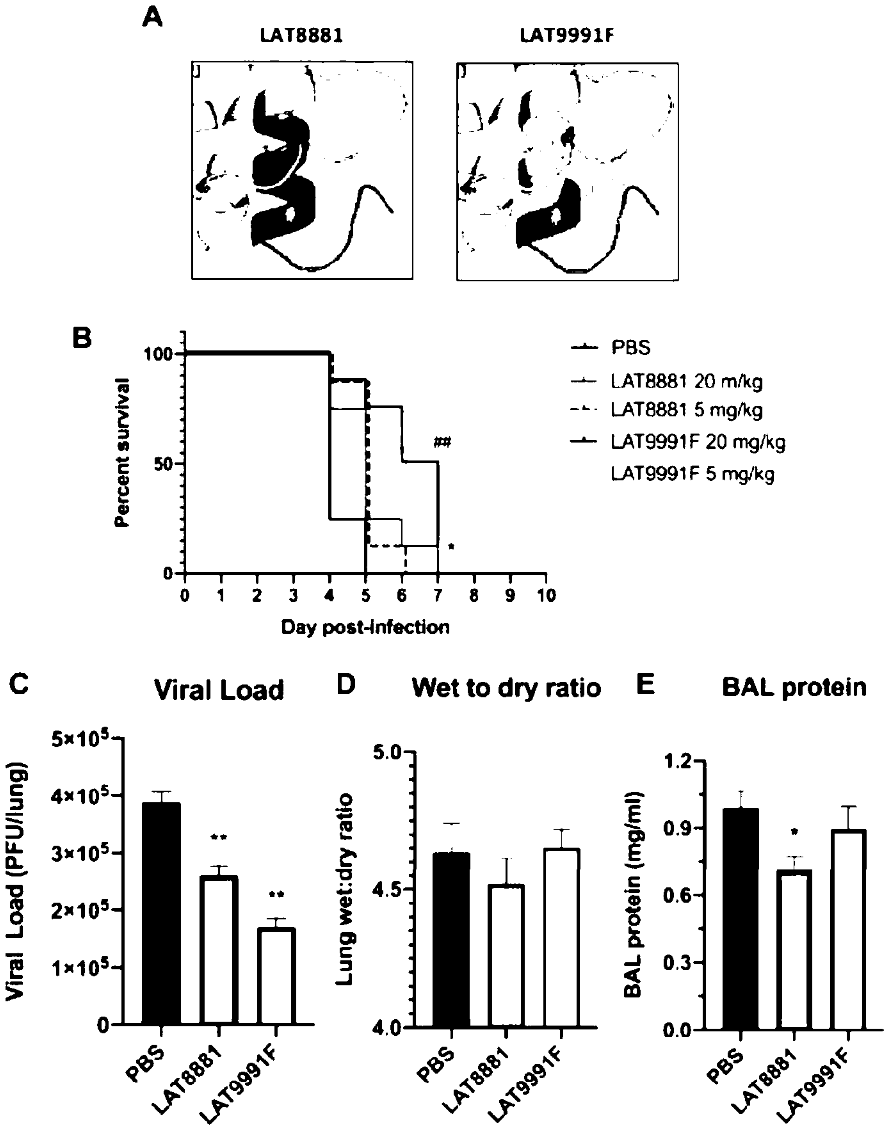
FIG. 4 shows that daily therapeutic treatment with LAT8881 or LAT9991F limits IAV replication and pathology. (A) Schematic of the structure of LAT8881 and its metabolite LAT9991F (red) derived from growth hormone (green). (B-E) Groups of 8 C57BL/6 mice were infected intranasally with 105 PFU of HKx31 IAV. (B) Mice were treated with LAT8881 or LAT9991F (5 or 20 mg/kg) via the intranasal route 24 hours following infection and then every 24 hours. IAV-infected control mice received PBS alone. Survival curves are shown. *p<0.05 HKx31 vs HKx31+LAT8881 20 mg/kg, ##p <0.01 HKx31 vs HKx31+LAT9991F 20 mg/kg Mantel-Cox log-rank test. (C-E) Mice were treated with LAT8881 or LAT9991F (20 mg/kg) via the intranasal route 24 hours following infection (day +1) and every 24 hours. IAV-infected control mice received PBS alone. On day 4 post-infection mice were euthanised. (C) Viral loads in the lung were measured by a standard plaque assay. (D) Lung tissue wet to dry ratios. (E) Total protein concentrations of cell-free bronchoalveolar lavage fluid. Data presented as the mean±SEM from 8 mice per group. *p<0.05, **p<0.01, HKx31 vs HKx31+LAT8881 or LAT9991F, One-way ANOVA.

Therapeutic Treatment with the LAT8881 Metabolite LAT9991F Improves Survival During Severe IAV Infection To further examine the pre-clinical therapeutic efficacy of naturally-occurring C-terminal fragments of GH, the ability of LAT8881 and its metabolite LAT9991F to limit severe IAV infection was evaluated using two different doses (FIG. 4A). Mice received intranasal LAT8881 or LAT9991F (5 or 20 mg/kg) 24 hours following infection with 105 PFU HKx31, with additional treatments at 48 hour intervals post-infection and control IAV-infected mice receiving PBS alone. Regardless of dose, LAT8881 and LAT9991F therapeutic treatment delayed IAV-associated lethality; however, only 20 mg/kg of either compound led to significant delays of 48-72 hours compared to controls (FIG. 4B). LAT7771, a peptide derived from the C-terminus of Prolactin that also shares a C—C constrained loop, had no significant effect on weight loss or survival of mice (n=16).

Daily LAT8881 and LAT9991F Therapeutic Treatment Limits Viral Replication and Pathology Following Severe IAV Infection.

The effect of daily administration of LAT8881 and LAT9991F from day 1 following IAV infection on viral loads, vascular leakage and immunopathology was examined. Consistent with previous results with prophylactic LAT8881 treatment (FIG. 2A), daily, therapeutic treatment with LAT8881 or LAT9991F (20 mg/kg) limited viral replication in the lungs, with a 1.5-fold or 2.4-fold reduction in levels of infectious virus on day 4 post-infection in lung tissues, respectively (FIG. 4C). Treatment of mice with LAT7771 did not significantly alter viral loads (n=8). While no significant differences were observed in lung wet-to-dry ratios in LAT8881- or LAT9991F-treated mice (FIG. 4D), LAT8881-treatment significantly reduced BAL fluid protein concentrations; an indication of reduced vascular leakage (FIG. 4E).

Daily LAT8881 and LAT9991F Therapeutic Treatment Limits Inflammation Following Severe IAV Infection.

Figure 5:
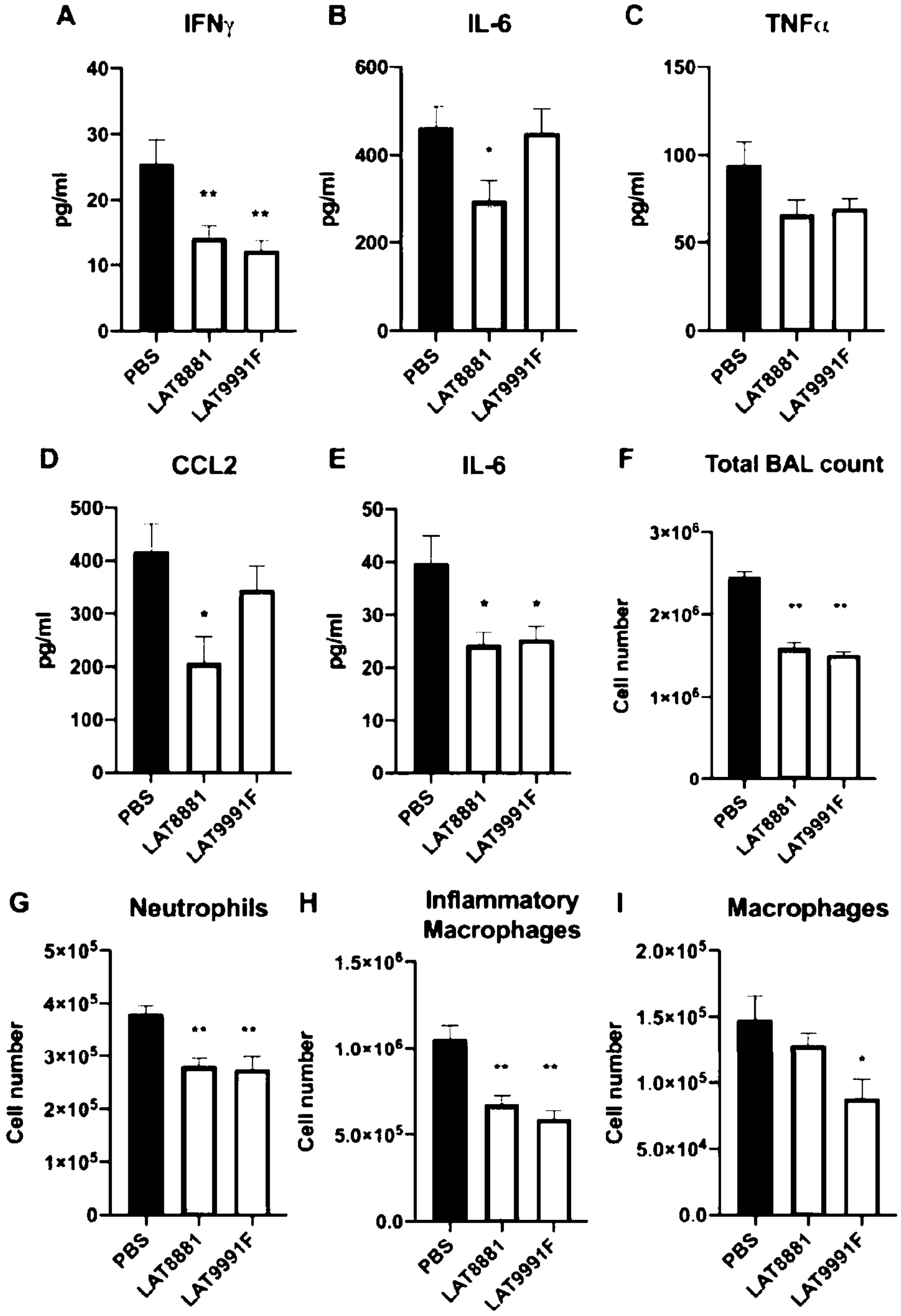
FIG. 5 shows that daily therapeutic treatment with LAT8881 or LAT9991F limits cellular infiltration and pro-inflammatory cytokine production. Groups of 8 C57BL/6 mice were infected intranasally with 105 PFU of HKx31 IAV. Mice were treated with LAT8881 or LAT9991F (20 mg/kg) via the intranasal route 24 hours following infection and then every 24 hours. IAV-infected control mice received PBS alone. On day 4 post-infection mice were euthanised. (A-D) Pro-inflammatory cytokine levels in BAL fluid were determined by CBA. (E) Levels of IL-6 in serum were determined by CBA. (F) Total numbers of leukocytes in BAL were determined by viable cell counts and (G-I) Ly6G+ neutrophils, total CD11c+ I-Ab low macrophages and Ly6C+ inflammatory macrophages in BAL were determined by flow cytometry. Data presented as the mean±SEM from 8 mice per group. *p<0.05, **p<0.01, HKx31 vs HKx31+LAT8881 or LAT9991F, One-way ANOVA.

Having established that prophylactic treatment of mice with LAT8881 reduces potentially deleterious inflammation (FIG. 2), an investigation was undertaken to determine whether daily therapeutic treatment with LAT8881 or LAT9991F would further alter cellular infiltration and production of pro-inflammatory cytokines at day 4 post-infection. Consistent with previous results (FIG. 2), treatment of IAV-infected mice with LAT8881 or LAT9991F every 24 hours from day 1 post-infection reduced levels of IFNγ in BAL fluid 2 to 2.3-fold, respectively (FIG. 5A). LAT8881 treatment significantly reduced IL-6 in the BAL fluid while a less profound reduction in TNFα levels was observed with administration of either compound (FIG. 5B-C). Interestingly, daily therapeutic LAT8881 treatment also limited levels of CCL2 in BAL fluid (FIG. 5D). Concentrations of IL-10, IL-12p70, as well as IFNα, IFNβ and IFN $\lambda_{2/3}$ in BAL fluid were not significantly different from PBS-treated infected animals. IL-6 in the serum was again significantly reduced, with approximately 1.6-fold reductions observed in LAT8881- and LAT9991F-treated mice (FIG. 5E). Total BAL cellularity was significantly reduced in LAT8881 and LAT9991F-treated mice (FIG. 5F) with significantly fewer neutrophils observed at day 4 post-infection (FIG. 5G). In contrast to previous findings with prophylactic treatment, treatment with LAT8881 and LAT9991F resulted in significantly fewer inflammatory Ly6C$^+$ macrophages in the airways (FIG. 5H), while LAT9991F reduced numbers of macrophages (FIG. 5I). Total numbers of dendritic cells were similar following treatment with either compound and comparable to PBS-treated infected controls. Collectively, treatment with LAT8881 or LAT9991F reduced concentration of several pro-inflammatory cytokines in the airways, decreased lung cellular infiltrates and limited serum IL-6 levels following severe IAV infection.

REFERENCES

Curtis M J, Alexander S, Cirino G, Docherty J R, George C H, Giembycz M A, et al. (2018). Experimental design and analysis and their reporting II: updated and simplified guidance for authors and peer reviewers. Br J Pharmacol 175: 987-993.

Rosli S, Kirby F J, Lawlor K E, Rainczuk K, Drummond G R, Mansell A, et al. (2019). Repurposing drugs targeting the $P2X_7$ receptor to limit hyperinflammation and disease during influenza virus infection. Br J Pharmacol 176: 3834-3844.

Tate M D, Deng Y M, Jones J E, Anderson G P, Brooks A G, & Reading P C (2009). Neutrophils ameliorate lung injury and the development of severe disease during influenza infection. J Immunol 183: 7441-7450.

Tate M D, Ong J D H, Dowling J K, McAuley J L, Robertson A B, Latz E, et al. (2016). Reassessing the role of the NLRP3 inflammasome during pathogenic influenza A virus infection via temporal inhibition. Sci Rep 6: 27912.

Tate M D, Pickett D L, van Rooijen N, Brooks A G, & Reading P C (2010). Critical role of airway macrophages in modulating disease severity during influenza virus infection of mice. J Virol 84: 7569-7580.

The claims defining the invention are as follows:

1. A method of treating a respiratory tract infection in a subject in need thereof, the method comprising administering to the subject in need thereof a therapeutically effective amount of a peptide of formula (I), or a pharmaceutically acceptable salt thereof:

(I)

$R^1$-CRSVEGSCG-$R^2$ (SEQ ID NO: 1)

wherein $R^1$ is selected from the group consisting of YLRIVQ (SEQ ID NO:45), LRIVQ (SEQ ID NO: 46), RIVQ (SEQ ID NO:47), IVQ, VQ, and Q, or $R^1$ is absent; and $R^2$ is F (phenylalanine) or $R^2$ is absent.

2. The method of claim 1, wherein the peptide is selected from the group consisting of YLRIVQCRSVEGSCGF (SEQ ID NO:2), LRIVQCRSVEGSCGF (SEQ ID NO: 3), CRSVEGSCG (SEQ ID NO:4) and CRSVEGSCGF (SEQ ID NO:5).

3. The method of claim 2, wherein the peptide is YLRIVQCRSVEGSCGF (SEQ ID NO: 2).

4. The method of claim 2, wherein the peptide is CRSVEGSCG (SEQ ID NO: 4).

5. The method of claim 2, wherein the peptide is CRSVEGSCGF (SEQ ID NO: 5).

6. The method of claim 1, wherein the subject is a human.

7. The method of claim 1, wherein the respiratory tract infection is a virus infection.

8. The method of claim 7, wherein the virus is selected from the group consisting of a picornavirus, a coronavirus, an influenza virus, a parainfluenza virus, a respiratory syncytial virus, an adenovirus, an enterovirus, or a metapneumovirus.

9. The method of claim 8, wherein the virus is an influenza virus or a coronavirus.

10. The method of claim 1, wherein the method comprises administering the peptide to the subject orally.

* * * * *